(12) United States Patent
Hukari et al.

(10) Patent No.: US 8,797,527 B2
(45) Date of Patent: Aug. 5, 2014

(54) BIOLOGIC FLUID SAMPLE ANALYSIS CARTRIDGE

(75) Inventors: Kyle Hukari, Ewing, NJ (US); Igor Nikonorov, Whitestone, NY (US); Ralph W. Dowdell, Trenton, NJ (US); Douglas Olson, Pipersville, PA (US); Niten V. Lalpuria, Mumbai (IN); Darryn Unfricht, Princeton, NJ (US); Benjamin Ports, Hamden, CT (US); Vu Phan, Princeton, NJ (US); Robin A. Levy, Southampton, PA (US); John W. Roche, Scarborough, ME (US)

(73) Assignee: Abbott Point of Care, Inc., Princeton, NJ (US)

( * ) Notice: Subject to any disclaimer, the term of this patent is extended or adjusted under 35 U.S.C. 154(b) by 0 days.

(21) Appl. No.: 13/594,439

(22) Filed: Aug. 24, 2012

(65) Prior Publication Data

US 2013/0114075 A1    May 9, 2013

Related U.S. Application Data

(60) Provisional application No. 61/527,114, filed on Aug. 24, 2011.

(51) Int. Cl.
*G01N 21/01*    (2006.01)
*G01N 33/50*    (2006.01)

(52) U.S. Cl.
CPC .......... *G01N 21/01* (2013.01); *B01L 2200/025* (2013.01); *B01L 2200/04* (2013.01)
USPC ................. 356/246; 422/68.1; 435/287.2

(58) Field of Classification Search
CPC .............. G01N 21/01; B01L 2200/025; B01L 2200/04

USPC .......... 356/244, 246; 422/68.1, 400, 430, 88; 435/287.2; 436/43, 168
See application file for complete search history.

(56) References Cited

U.S. PATENT DOCUMENTS

| | | | |
|---|---|---|---|
| 3,447,863 | A | 6/1969 | Patterson |
| 3,883,247 | A | 5/1975 | Adams |
| 3,895,661 | A | 7/1975 | Praglin et al. |

(Continued)

FOREIGN PATENT DOCUMENTS

| | | | |
|---|---|---|---|
| EP | 0381501 | 8/1990 | |
| EP | 0638799 | 2/1995 | ........................ 21/5 |

(Continued)

OTHER PUBLICATIONS

International search report for PCT/US2012/052286 dated Jan. 30, 2013.

*Primary Examiner* — Sang Nguyen
(74) *Attorney, Agent, or Firm* — O'Shea Getz P.C.

(57) ABSTRACT

A biological fluid sample analysis cartridge, analysis system, and method for analyzing a biologic fluid sample are provided. The cartridge includes a collection port, at least one channel within the cartridge in fluid communication with the collection port, a passage in fluid communication with the at least one channel, and an analysis chamber mounted on a tray. The tray is mounted relative to the cartridge and selectively positionable relative to the passage in a first position where the analysis chamber will engage a bolus of sample extending out from the passage to permit selective transfer of sample from the bolus to the analysis chamber.

30 Claims, 11 Drawing Sheets

(56) References Cited

U.S. PATENT DOCUMENTS

| | | |
|---|---|---|
| 3,916,205 A | 10/1975 | Kleinerman |
| 3,925,166 A | 12/1975 | Blume |
| 4,088,448 A | 5/1978 | Lilja et al. |
| 4,171,866 A | 10/1979 | Tolles |
| 4,264,560 A | 4/1981 | Natelson |
| 4,427,294 A | 1/1984 | Nardo |
| 4,550,417 A | 10/1985 | Nunogaki et al. |
| 4,558,014 A | 12/1985 | Hirschfeld et al. |
| 4,596,035 A | 6/1986 | Gershman et al. |
| 4,689,307 A | 8/1987 | Schwartz |
| 4,790,640 A | 12/1988 | Nason |
| 4,853,210 A | 8/1989 | Kass |
| 4,902,624 A | 2/1990 | Columbus et al. |
| 4,911,782 A | 3/1990 | Brown |
| 4,950,455 A | 8/1990 | Smith |
| 5,028,529 A | 7/1991 | Ericcson |
| 5,122,284 A | 6/1992 | Braynin et al. |
| 5,132,097 A | 7/1992 | Van Deusen et al. |
| 5,169,601 A | 12/1992 | Ohta et al. |
| 5,184,188 A | 2/1993 | Bull et al. |
| 5,223,219 A | 6/1993 | Subramanian et al. |
| 5,275,951 A | 1/1994 | Chow et al. |
| 5,281,540 A | 1/1994 | Merkh et al. |
| 5,316,952 A | 5/1994 | Brimhall |
| 5,362,648 A | 11/1994 | Koreyasu et al. |
| 5,376,252 A | 12/1994 | Ekstrom et al. |
| 5,397,479 A | 3/1995 | Kass et al. |
| 5,427,959 A | 6/1995 | Nishimura et al. |
| 5,431,880 A | 7/1995 | Kramer |
| 5,472,671 A | 12/1995 | Nilsson et al. |
| 5,482,829 A | 1/1996 | Kass et al. |
| 5,503,803 A | 4/1996 | Brown |
| 5,538,691 A | 7/1996 | Tosa et al. |
| 5,547,849 A | 8/1996 | Baer et al. |
| 5,585,246 A | 12/1996 | Dubrow et al. |
| 5,591,403 A | 1/1997 | Gavin et al. |
| 5,608,519 A | 3/1997 | Gourley et al. |
| 5,623,415 A | 4/1997 | O'Bryan et al. |
| 5,627,041 A | 5/1997 | Shartle |
| 5,638,828 A | 6/1997 | Lauks et al. |
| 5,641,458 A | 6/1997 | Shockley, Jr. et al. |
| 5,646,046 A | 7/1997 | Fischer |
| 5,674,457 A | 10/1997 | Williamsson et al. |
| 5,681,529 A | 10/1997 | Taguchi et al. |
| 5,768,407 A | 6/1998 | Shen et al. |
| 5,781,303 A | 7/1998 | Berndt |
| 5,787,189 A | 7/1998 | Lee et al. |
| 5,800,781 A | 9/1998 | Gavin et al. |
| 5,879,628 A | 3/1999 | Ridgeway et al. |
| 5,939,326 A | 8/1999 | Chupp et al. |
| 5,948,686 A | 9/1999 | Wardlaw |
| 5,968,453 A | 10/1999 | Shugart |
| 5,985,218 A | 11/1999 | Goodale |
| 6,004,821 A | 12/1999 | Levine et al. |
| 6,016,367 A | 1/2000 | Benedetti et al. |
| 6,016,712 A | 1/2000 | Warden et al. |
| 6,022,734 A | 2/2000 | Wardlaw |
| 6,106,778 A | 8/2000 | Oku et al. |
| 6,130,098 A | 10/2000 | Handique et al. |
| 6,150,178 A | 11/2000 | Cesarczyk et al. |
| 6,176,962 B1 | 1/2001 | Soane et al. |
| 6,188,474 B1 | 2/2001 | Dussault et al. |
| 6,235,536 B1 | 5/2001 | Wardlaw |
| 6,261,519 B1 | 7/2001 | Harding et al. |
| 6,365,111 B1 | 4/2002 | Bass |
| 6,395,232 B1 | 5/2002 | McBride |
| 6,420,114 B1 | 7/2002 | Bedilion et al. |
| 6,448,090 B1 | 9/2002 | McBride |
| 6,468,807 B1 | 10/2002 | Svensson et al. |
| 6,521,182 B1 | 2/2003 | Shartle et al. |
| 6,537,501 B1 | 3/2003 | Holl et al. |
| 6,544,793 B2 | 4/2003 | Berndt |
| 6,551,554 B1 | 4/2003 | Vermeiden et al. |
| 6,573,988 B1 | 6/2003 | Thomsen et al. |
| 6,576,194 B1 | 6/2003 | Holl et al. |
| 6,597,438 B1 | 7/2003 | Cabuz et al. |
| 6,613,286 B2 | 9/2003 | Braun, Sr. et al. |
| 6,613,529 B2 | 9/2003 | Bedilion et al. |
| 6,623,701 B1 | 9/2003 | Eichele et al. |
| 6,656,431 B2 | 12/2003 | Holl et al. |
| 6,712,925 B1 | 3/2004 | Holl et al. |
| 6,723,290 B1 | 4/2004 | Wardlaw |
| 6,766,817 B2 | 7/2004 | da Silva |
| 6,783,736 B1 | 8/2004 | Taylor et al. |
| 6,838,055 B2 | 1/2005 | Sando et al. |
| 6,852,284 B1 | 2/2005 | Holl et al. |
| 6,866,823 B2 | 3/2005 | Wardlaw |
| 7,000,330 B2 | 2/2006 | Schwichtenberg et al. |
| 7,010,391 B2 | 3/2006 | Handique et al. |
| 7,220,593 B2 | 5/2007 | Haubert et al. |
| 7,226,562 B2 | 6/2007 | Holl et al. |
| 7,277,166 B2 | 10/2007 | Padmanabhan et al. |
| 7,329,538 B2 | 2/2008 | Wainwright et al. |
| 7,351,379 B2 | 4/2008 | Schleifer |
| 7,364,699 B2 | 4/2008 | Charlton |
| 7,381,374 B2 | 6/2008 | Tsai et al. |
| 7,468,160 B2 | 12/2008 | Thompson et al. |
| 7,641,856 B2 | 1/2010 | Padmanabhan et al. |
| 7,671,974 B2 | 3/2010 | O'Mahony et al. |
| 7,731,901 B2 | 6/2010 | Wardlaw |
| 7,738,094 B2 | 6/2010 | Goldberg |
| 7,744,819 B2 | 6/2010 | Berndtsson et al. |
| 7,794,669 B2 | 9/2010 | Gyonouchi et al. |
| 7,802,467 B2 | 9/2010 | Wang |
| 7,871,813 B2 | 1/2011 | Wyatt et al. |
| 7,903,241 B2 * | 3/2011 | Wardlaw et al. ............... 356/39 |
| 7,929,122 B2 | 4/2011 | Wardlaw et al. |
| 7,951,337 B2 | 5/2011 | Vollert |
| 7,951,599 B2 | 5/2011 | Levine et al. |
| 7,976,789 B2 | 7/2011 | Kenis et al. |
| 7,978,329 B2 | 7/2011 | Padmanabhan et al. |
| 8,025,854 B2 | 9/2011 | Ohman et al. |
| 8,033,162 B2 | 10/2011 | Wang |
| 8,071,051 B2 | 12/2011 | Padmanabhan et al. |
| 8,092,758 B2 | 1/2012 | Lindberg et al. |
| 8,097,225 B2 | 1/2012 | Padmanabhan et al. |
| 8,133,738 B2 | 3/2012 | Levine et al. |
| 8,158,434 B2 | 4/2012 | Wardlaw |
| 8,163,165 B2 | 4/2012 | Offenbacher et al. |
| 8,173,380 B2 | 5/2012 | Yang et al. |
| 8,182,763 B2 * | 5/2012 | Duffy et al. ................ 422/500 |
| 2002/0025279 A1 | 2/2002 | Weigl |
| 2003/0012697 A1 | 1/2003 | Hahn et al. |
| 2003/0178641 A1 | 9/2003 | Blair et al. |
| 2006/0160164 A1 | 7/2006 | Miller et al. |
| 2007/0025876 A1 | 2/2007 | Nishijima et al. |
| 2007/0036679 A1 | 2/2007 | Munenaka |
| 2007/0111302 A1 | 5/2007 | Handique et al. |
| 2007/0243117 A1 | 10/2007 | Wardlaw |
| 2007/0254372 A1 | 11/2007 | Bickel et al. |
| 2008/0176253 A1 | 7/2008 | Christodoulides et al. |
| 2008/0200343 A1 | 8/2008 | Clemens et al. |
| 2009/0011518 A1 | 1/2009 | Lindberg |
| 2009/0156966 A1 | 6/2009 | Kontschieder et al. |
| 2009/0286327 A1 | 11/2009 | Cho et al. |
| 2010/0021456 A1 | 1/2010 | Miossec et al. |
| 2010/0151565 A1 | 6/2010 | De Gier et al. |
| 2010/0175999 A1 | 7/2010 | Barlow et al. |
| 2010/0189338 A1 | 7/2010 | Lin et al. |
| 2010/0209304 A1 | 8/2010 | Sarofim |
| 2010/0210029 A1 * | 8/2010 | Meinhart et al. ............. 436/168 |
| 2011/0044862 A1 | 2/2011 | Chang et al. |
| 2011/0164803 A1 | 7/2011 | Wang et al. |
| 2011/0192219 A1 | 8/2011 | Miyamura |
| 2011/0194977 A1 | 8/2011 | Miyamura et al. |
| 2011/0201099 A1 * | 8/2011 | Anderson et al. ........... 435/287.2 |
| 2011/0206557 A1 * | 8/2011 | Phan et al. .................. 422/68.1 |
| 2011/0214745 A1 | 9/2011 | Zhou et al. |
| 2011/0244581 A1 * | 10/2011 | Nikonorov et al. ............ 436/43 |
| 2011/0244593 A1 * | 10/2011 | Wardlaw ...................... 436/180 |
| 2011/0293489 A1 | 12/2011 | Zhou et al. |

(56) References Cited

U.S. PATENT DOCUMENTS

2012/0004139 A1 1/2012 Staker
2012/0034647 A1 2/2012 Herzog et al.
2012/0082599 A1 4/2012 Weber

FOREIGN PATENT DOCUMENTS

| | | | |
|---|---|---|---|
| EP | 0778950 | 6/1997 | |
| EP | 0788604 | 8/1997 | |
| EP | 1245279 | 10/2002 | |
| EP | 1701150 | 9/2006 | |
| EP | 1932594 | 6/2008 | |
| EP | 2040839 | 4/2009 | |
| EP | 1390750 | 3/2011 | |
| EP | 2322276 | 5/2011 | |
| EP | 2050498 | 3/2012 | |
| WO | WO 95/11454 | 4/1995 | ................... 33/50 |
| WO | 9624876 | 8/1996 | |
| WO | 9945386 | 9/1999 | |
| WO | 0132828 | 5/2001 | |
| WO | 2005100539 | 10/2005 | |
| WO | 2005111580 | 11/2005 | |
| WO | 2005114142 | 12/2005 | |
| WO | 2006124821 | 11/2006 | |
| WO | 2007047908 | 4/2007 | |
| WO | 2007075922 | 7/2007 | |
| WO | 2007084232 | 7/2007 | |
| WO | 2007112332 | 10/2007 | |
| WO | 2008079616 | 7/2008 | |
| WO | 2008087405 | 7/2008 | |
| WO | 2008157795 | 12/2008 | |
| WO | 2009117652 | 9/2009 | |
| WO | 2009117664 | 9/2009 | |
| WO | 2009117682 | 9/2009 | |
| WO | 2009117683 | 9/2009 | |
| WO | 2009124179 | 10/2009 | |
| WO | 2009124186 | 10/2009 | |
| WO | 2009124190 | 10/2009 | |
| WO | 2009126505 | 10/2009 | |
| WO | 2009126800 | 10/2009 | |
| WO | 2011075667 | 6/2011 | |
| WO | 2011082342 | 7/2011 | |
| WO | 2011116305 | 9/2011 | |
| WO | 2012004723 | 1/2012 | |
| WO | 2012019118 | 2/2012 | |

\* cited by examiner

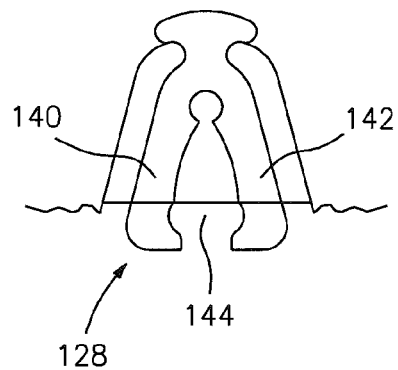 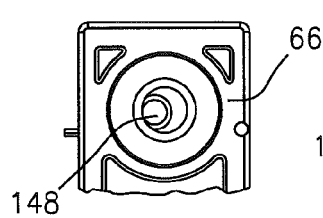 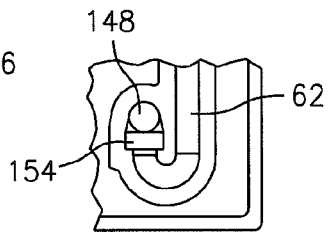
FIG. 12  FIG. 13  FIG. 14
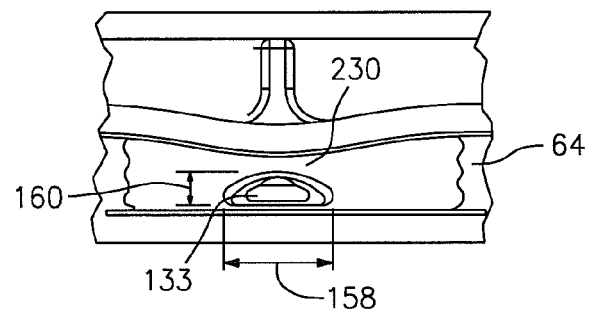
FIG. 15
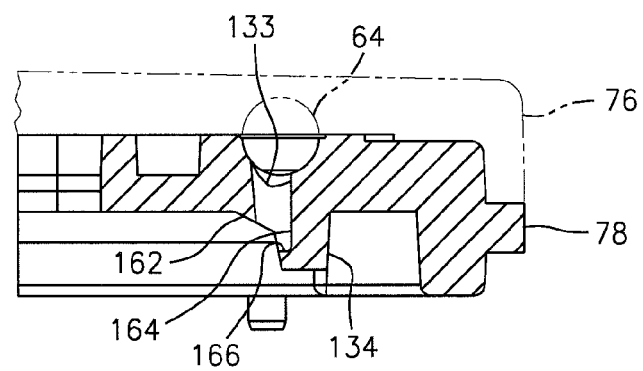
FIG. 16

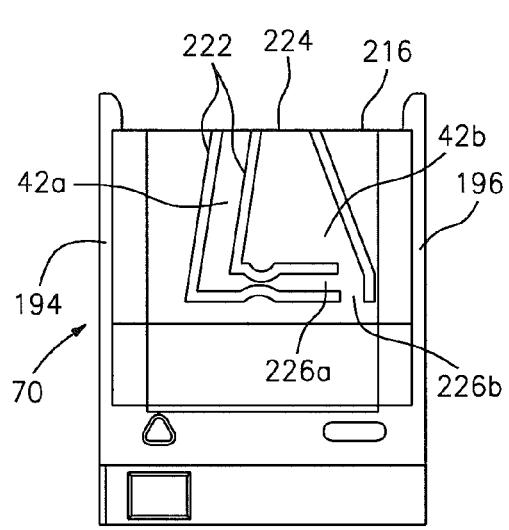 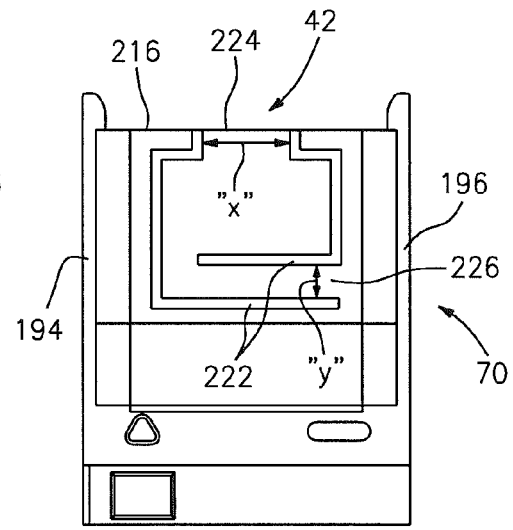
FIG. 25    FIG. 26
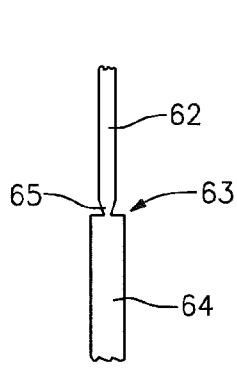 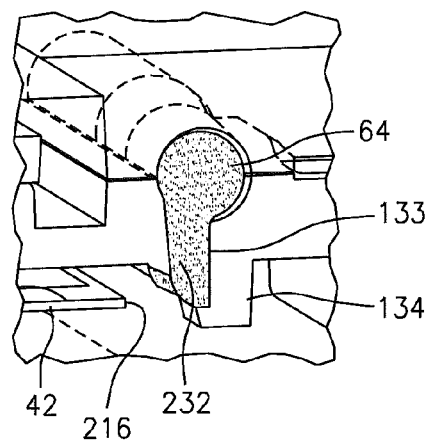
FIG. 35    FIG. 27

US 8,797,527 B2

BIOLOGIC FLUID SAMPLE ANALYSIS CARTRIDGE

The present application is entitled to the benefit of and incorporates by reference essential subject matter disclosed in the U.S. Provisional Patent Application Ser. No. 61/527,114, filed Aug. 24, 2011.

BACKGROUND OF THE INVENTION

1. Technical Field

The present invention relates to apparatus for biologic fluid analyses in general, and to cartridges for acquiring, processing, and containing biologic fluid samples for analysis in particular.

2. Background Information

Historically, biologic fluid samples such as whole blood, urine, cerebrospinal fluid, body cavity fluids, etc. have had their particulate or cellular contents evaluated by smearing a small undiluted amount of the fluid on a slide and evaluating that smear under a microscope. Reasonable results can be gained from such a smear, but the cell integrity, accuracy and reliability of the data depends largely on the technician's experience and technique.

In some instances, constituents within a biological fluid sample can be analyzed using impedance or optical flow cytometry. These techniques evaluate a flow of diluted fluid sample by passing the diluted flow through one or more orifices located relative to an impedance measuring device or an optical imaging device. A disadvantage of these techniques is that they require dilution of the sample, and fluid flow handling apparatus.

What is needed is an apparatus for evaluating a sample of substantially undiluted biologic fluid, one capable of providing accurate results, one that does not require sample fluid flow during evaluation, one that can perform particulate component analyses, and one that is cost-effective.

DISCLOSURE OF THE INVENTION

According to an aspect of the present invention, a biological fluid sample analysis cartridge is provided that includes a collection port, at least one channel within the cartridge in fluid communication with the collection port, a passage in fluid communication with the at least one channel, and an analysis chamber mounted on a tray. The tray is mounted relative to the cartridge and selectively positionable relative to the passage in a first position where the analysis chamber will engage a bolus of sample extending out from the passage to permit selective transfer of sample from the bolus to the analysis chamber.

In an embodiment of this aspect, the passage includes a first end and a second end, and the first end is in fluid communication with the at least one channel, and the second end is configured to permit the formation of a bolus of sample extending out from the second end.

In another embodiment of this aspect, the analysis chamber includes a base chamber panel and an upper chamber panel, separated from one another by a chamber height, and each of the panels includes a sample entry edge.

In another embodiment of the aspect, a first end of the passage has a slot configuration with a major axis and a minor axis, wherein the major axis is larger than the minor axis.

In another embodiment of the aspect, the passage is at least partially disposed within an interface post.

In another embodiment of the aspect, the tray is operable to reside in a second position within the cartridge, and in the second position the analysis chamber is separated from the passage.

In another embodiment of the aspect, a biasing structure (e.g., a tray clip) maintains the tray in the second position, and in the first position the biasing structure biases the tray toward the second position.

In another embodiment of the aspect, the analysis chamber is defined by a base chamber panel, an upper chamber panel, and a plurality of lateral boundaries, and wherein the lateral boundaries form a first opening and second opening, and wherein the first opening is larger than the second opening. The lateral boundaries may be configured to create a circuitous path between the first opening and the second opening, and/or may form a plurality of sub-chambers.

In another embodiment of the aspect, the cartridge includes a secondary analysis chamber in fluid communication with the at least one channel.

In another embodiment of the aspect, the at least one channel includes an initial channel in fluid communication with the collection port, and a secondary channel having a first end in fluid communication with the initial channel and a second end in fluid communication with the passage. The initial channel has a cross-sectional area sized such that sample travels by capillary force within the initial channel and the secondary channel has a cross-sectional area sized such that sample cannot travel by capillary force within the secondary channel.

In another embodiment of the aspect, the cartridge includes a fluid actuator port configured to engage a sample motion system and to permit a fluid motive force to access the cartridge to cause the movement of fluid sample within the at least one channel.

In another embodiment of the aspect, the cartridge includes an analysis chamber window configured to allow visual inspection of the analysis chamber disposed in the first position.

According to another aspect of the present invention, a biological fluid sample analysis cartridge is provided that includes a collection port, at least one channel within the cartridge in fluid communication with the collection port, and an analysis chamber defined by a base chamber panel, an upper chamber panel, and a plurality of lateral boundaries. The lateral boundaries form a first opening and second opening, and wherein the first opening is larger than the second opening. The base chamber panel has an interior surface, and the upper chamber panel has an interior surface, and at least one of the lateral boundaries contacts both interior surfaces.

In an embodiment of the aspect, the lateral boundaries are configured to create a circuitous path between the first opening and the second opening, and/or form a plurality of sub-chambers within the analysis chamber.

According to another aspect of the present invention, a biologic fluid analysis system is provided that includes an analysis device and a biological fluid sample analysis cartridge. The analysis device has an objective lens, at least one sample illuminator, at least one image dissector, a tray actuation device, and a programmable analyzer. The biological fluid sample analysis cartridge includes a collection port, at least one channel within the cartridge in fluid communication with the collection port, a passage in fluid communication with the at least one channel, and an analysis chamber mounted on a tray. The tray is mounted relative to the cartridge and selectively positionable relative to the passage via the tray actuation device in a first position where the analysis chamber will engage a bolus of sample extending out from the passage to permit selective transfer of sample from the bolus to the analysis chamber.

According to another aspect of the present invention, a method for analyzing a biologic fluid sample is provided. The method includes the steps of: a) providing an automated analysis device having a tray actuation device, and a programmable analyzer; b) providing a biological fluid sample analysis cartridge that includes a collection port, at least one channel within the cartridge in fluid communication with the collection port, a passage in fluid communication with the at least one channel, and an analysis chamber mounted on a tray, which tray is mounted relative to the cartridge and selectively positionable relative to the passage via the tray actuation device in a first position where the analysis chamber may engage a bolus of sample extending out from the passage; c) moving the biologic fluid sample into the passage to create the bolus of fluid sample extending out from the passage; d) positioning the tray relative to the cartridge so that the analysis chamber will engage the bolus of sample and permit selective transfer of sample from the bolus to the analysis chamber; e) removing the tray from the cartridge using the tray actuation device; f) imaging the sample quiescently residing within the analysis chamber to produce one or more images of the sample; and g) analyzing the sample using the one or more images of the sample.

The present invention is described herein in terms of aspects and embodiments of those aspects that include elements or features that may be included with the aspects. The identified embodiments may be included with the aspect of the invention singularly or in combination with any of the other identified embodiments as will be described herein below in the Detailed Description. The features and advantages of the present invention will become apparent in light of the detailed description of the invention provided below, and as illustrated in the accompanying drawings.

BRIEF DESCRIPTION OF THE DRAWINGS

FIG. 12 is a partial planar view of the center panel of FIG. 10, showing a tray clip.

FIG. 13 is a partial planar view of the center panel of FIG. 11, showing a fluid actuator port.

FIG. 14 is a partial planar view of the center panel of FIG. 10, showing a passage to the fluid actuator port.

FIG. 15 is a partial planar view of the center panel of FIG. 10, showing a portion of the mixing tube including a dispense tube passage.

FIG. 16 is a partial sectional view of the center panel of FIG. 10, cut along sectional line 16-16.

FIGS. 25 and 26 are each planar views of a tray embodiment, each illustrating a different configuration of lateral boundaries within an analysis chamber.

FIG. 27 is a diagrammatic sectional view of the present cartridge, illustrating a configuration of the analysis chamber and a chamber interface post 134 wherein the edges of the analysis chamber are not engaged with a sample bolus bulging out from the post.

FIG. 35 is a diagrammatic view of a constricted section of the initial channel.

DETAILED DESCRIPTION

Figure 1:
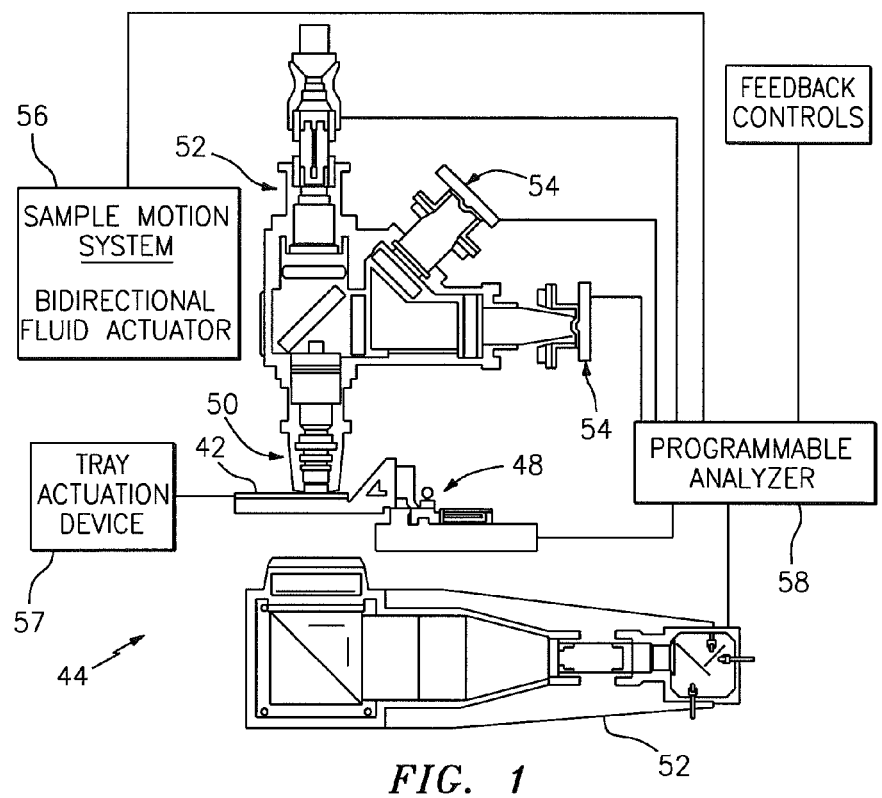
FIG. 1 diagrammatically illustrates a biologic fluid analysis device.
Figure 2:
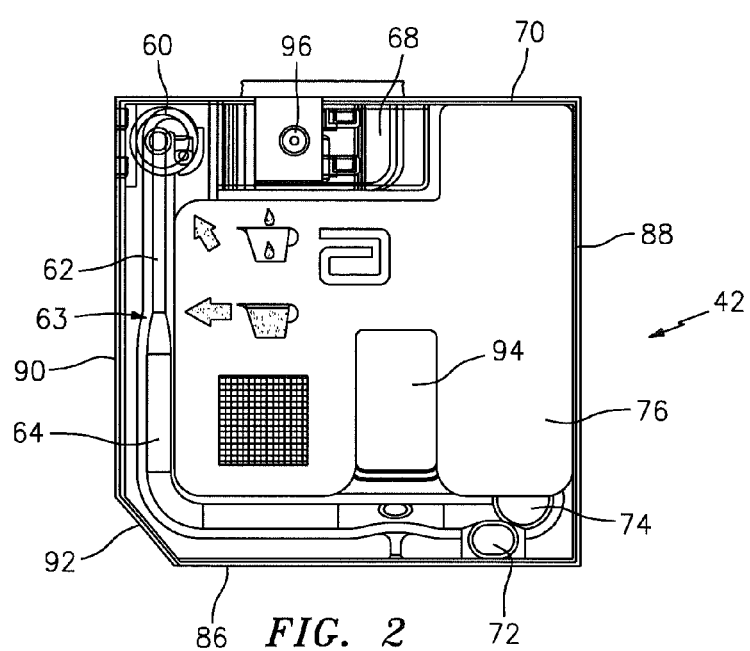
FIG. 2 is a planar view of an embodiment of the present cartridge.

Referring to FIGS. 1 and 2, the present biologic fluid sample cartridge 40 is operable to receive a biologic fluid sample such as a whole blood sample or other biologic fluid specimen and subsequently hold at least a portion of that sample within an analysis chamber 42. The cartridge 40 is configured for use in an automated analysis device 44, wherein the sample can be manipulated within the cartridge 40 and subsequently analyzed. An example of an analysis device 44 is schematically shown in FIG. 1. The device includes a cartridge holding and manipulating device 48, a sample objective lens 50, a plurality of sample illuminators 52, an image dissector(s) 54, a sample motion system 56, a tray actuation device 57, and a programmable analyzer 58.

One or both of the objective lens 50 and cartridge holding device 48 are movable toward and away from each other to change a relative focal position. The sample illuminators 52 illuminate the sample using light along predetermined wavelengths. Light transmitted through the sample, or fluoresced from the sample, is captured using the image dissector 54, and a signal representative of the captured light is sent to the programmable analyzer 58, where it is processed into an image. The tray actuation device 57 is operable to selectively move a tray component of the cartridge 40 (as will be described below) relative to the remainder of the cartridge 40. The tray actuation device 57 may include linear actuators and mechanical linkages, or the like.

The programmable analyzer 58 includes a central processing unit or other device operable to carry out functions including: 1) perform the instructions of a computer program: 2) perform basic arithmetical and/or logical functions; and 3), perform input/output operations of the analyzer, etc. The analyzer 58 is in communication with the cartridge holding and manipulating device 48, the sample illuminators 52, the image dissector 54, the sample motion system 56, and the tray actuation device 57. The analyzer 58 is adapted (e.g., programmed) to receive the signals and selectively perform the functions necessary to operate the cartridge holding and manipulating device 48, the sample illuminator 52, the image dissector 54, the sample motion system 56, and the tray actuation device 57. The sample motion system 56 includes a bidirectional fluid actuator and a cartridge interface. The bidirectional fluid actuator is operable to produce fluid motive forces that can move fluid sample (e.g., a sample bolus) within channels disposed in the cartridge 40 in either axial direction (i.e., back and forth). The term "sample bolus" is used herein to refer to a continuous body of fluid sample disposed within the cartridge 40; e.g., a continuous body of fluid sample disposed within a cartridge channel that fills a cross-section of the channel, which cross-section is perpendicular to the axial length of the channel. An example of an acceptable bidirectional fluid actuator is a piezo bending disk type pump, utilized with a driver for controlling the fluid actuator.

The analysis devices described in U.S. Pat. No. 6,866,823 and U.S. patent application Ser. Nos. 13/077,476 and 13/204,415 (each of which is hereby incorporated by reference in its entirety) are examples of acceptable types of analysis device 44 for use with the present cartridge 40. The present cartridge 40 is not limited to use with these analysis devices, however.

Figure 3:
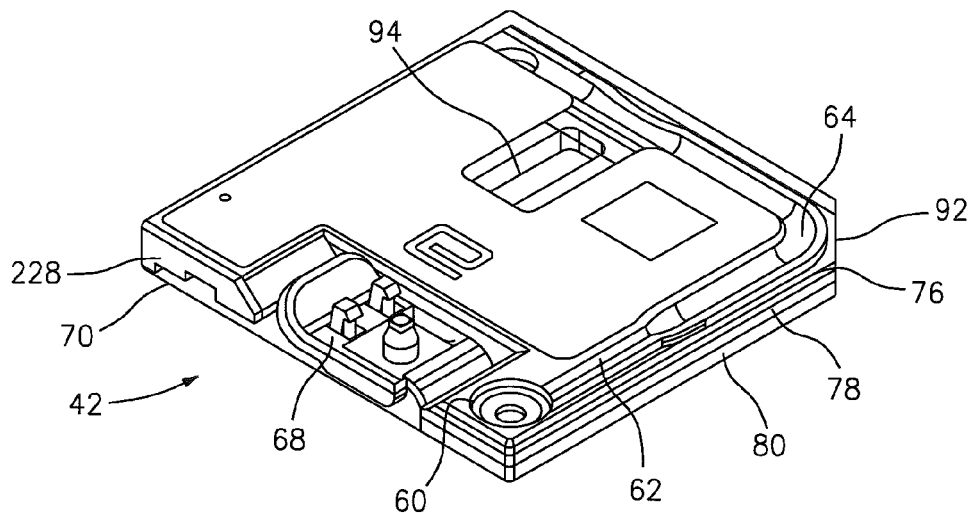
FIG. 3 is a perspective view of an embodiment of the present cartridge.
Figure 4:
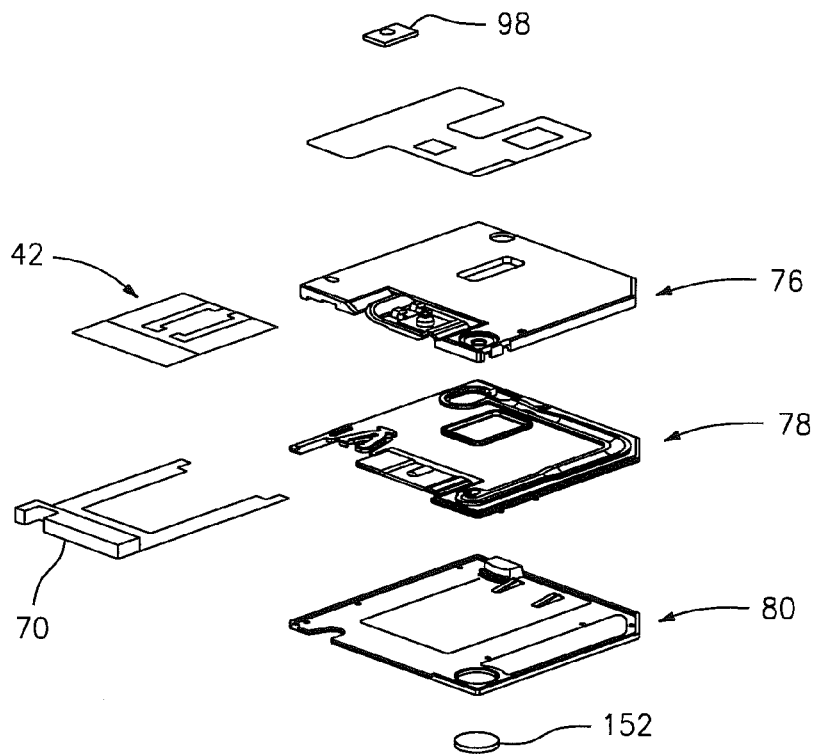
FIG. 4 is an exploded, perspective view of an embodiment of the present cartridge.

Referring to FIGS. 2-4, the cartridge 40 includes a collection port 60, an initial channel 62, a secondary channel 64, an analysis chamber 42, and a fluid actuator port 66. The collection port 60 is in fluid communication with the initial channel 62, and the initial channel 62, in turn, is in fluid communication with the secondary channel 64. A chamber fluid passage (e.g., passage 133 shown in FIG. 16) provides a path to the analysis chamber 42 from the secondary channel 64, permitting selective distribution of sample to the analysis chamber 42 as will be explained below. In some embodiments, the cartridge 40 includes structure for covering and sealing within the collection port 60; e.g., a collection port cap 68 hingedly attached to the cartridge 40 which can be pivotally engaged with the collection port 60. The present cartridge 40 is not limited to sealing the collection port 60 with a hinged cap, however; e.g., a cap that slides into and out of engagement with the port can be used.

In some embodiments, the analysis chamber 42 is attached to a tray 70 that, as will be described below, is selectively moveable relative to the remainder of the cartridge 40; e.g., the tray 70 may be moved partially or completely out of the cartridge 40 for imaging. The cartridge 40 is not limited, however, to embodiments where the analysis chamber 42 is mounted on a movable tray 70. In some embodiments, the cartridge 40 may include one or both of a secondary analysis chamber 72 and an excess sample reservoir 74.

The cartridge 40 can be formed as a unitary structure or can be formed from a plurality of components. The cartridge 40 embodiment shown in FIGS. 3 and 4 includes a top panel 76, a center panel 78, a base panel 80, and a tray 70.

Referring to FIGS. 5-9, the top panel 76 includes an outer surface 82, an inner surface 84, a front edge 86, a first side edge 88, a second side edge 90, a notch edge 92, an analysis chamber window 94, the collection port 60, and the port cap 68. The top panel 76 embodiment shown in FIGS. 5 and 6 includes a portion of a secondary analysis chamber 72 and a portion of an excess sample reservoir 74. In a preferred embodiment, the top panel 76 is made from a clear polymeric material; e.g., Lexan® brand polycarbonate. The analysis chamber window 94 may be a void (i.e., an opening) or may include a clear pane that covers the window but allows visual inspection through the window. In a preferred embodiment shown in FIGS. 5 and 6, the analysis chamber window 94 is a transparent window located at a level that is lower than the surrounding outer surface 82, and has a width that is less than the typical width of an end-user's finger. The lowered and narrowed window helps to prevent contact between the end-user's finger (and any dirt or debris that may be on that finger) and the transparent window 94. The notch edge 92, which is shown as a straight edge extending between the front edge 86 and the second side edge 90, makes the cartridge 40 asymmetric to facilitate correct orientation of the cartridge 40 during loading into the analysis device 44. The notch edge 92 is not limited to a straight configuration. The port cap 68 shown in FIGS. 5 and 8 includes a stopper 96, an absorbent pad 98, and a latch mechanism 100 operable to hold the port cap 68 in an engaged position with the collection port 60. In a preferred embodiment, the stopper 96 is configured to seal a passage 102 between the collection port 60 and the initial channel 62, and thereby prevent any transfer of sample into or out of the initial channel 62 via the port 60 once the initial channel 62 is filled.

Figure 6:
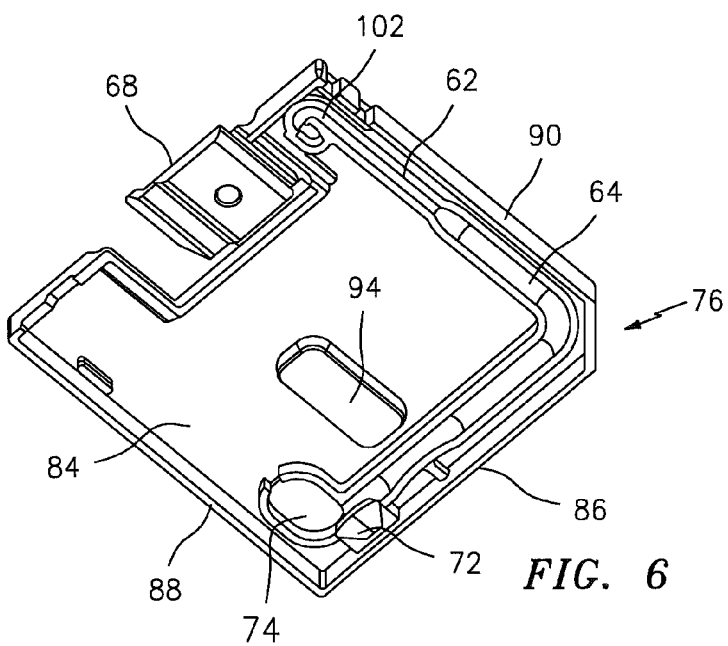
FIG. 6 is a perspective view of the top panel of FIG. 5, showing the opposite surface of the panel.
Figure 7:
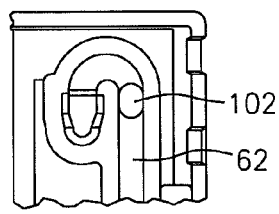
FIG. 7 is a partial planar view of the top panel of FIG. 5, showing a portion of the initial channel
Figure 8:
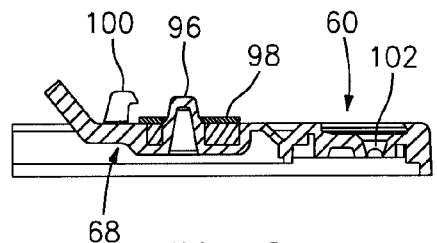
FIG. 8 is a partial sectional view of the top panel of FIG. 5, cut along sectional line 8-8.

In the top panel perspective view shown in FIG. 5, the top panel outer surface 82 is shown, including the collection port 60 open to the outer surface 82, the passage 102 (referred to hereinafter as the "drain tube 102") between the collection port 60 and the initial channel 62, the analysis chamber window 94, the secondary analysis chamber 72, and the port cap 68 oriented in an open position. In FIGS. 6-8, the top panel inner surface 84 is shown, including a portion of the initial channel 62, the drain tube 102, a portion of the secondary channel 64, the analysis chamber window 94, a portion of the secondary analysis chamber 72, a portion of the excess sample reservoir 74, and the collection port cap 68. As will be explained below, the portions of the initial channel 62, secondary channel 64, excess sample reservoir 74, etc., not included in the top panel 76, are included in the center panel 78. The aforesaid channels and passages are collectively formed by the portions thereof (i.e., in the top panel 76 and center panel 78), when the two panels 76, 78 are joined together. Also as will be explained below, a portion of the secondary analysis chamber 72 is included in the base panel 80. The secondary analysis chamber 72 is formed by the portions thereof (i.e., in the top panel 76 and the base panel 80), when the two panels 76, 80 are joined together. The degree to which a channel or passage may be formed in one or the other of the top panel 76 and center panel 78 can vary; e.g., 50% of the channel cross-sectional area (normal to axial) can be formed by structure in one of the base plate or upper panel, and the other 50% in the other; or 70% in one and 30% in the other, etc.

The collection port 60 is configured to accept a fluid sample from a container (e.g., deposited by needle, etc.) and/or from a surface source (e.g., a finger prick). The collection port 60 has a concave shape that facilitates gravity collection of the sample from the port 60 into the drain tube 102. The drain tube 102 may be sized to draw sample out of the collection port 60 by capillary force, or by gravity, or some combination thereof. The collection port 60 holds enough sample for the application at hand; e.g., for a blood sample analysis, a bowl volume of approximately 60 µl typically will be adequate.

Figure 5:
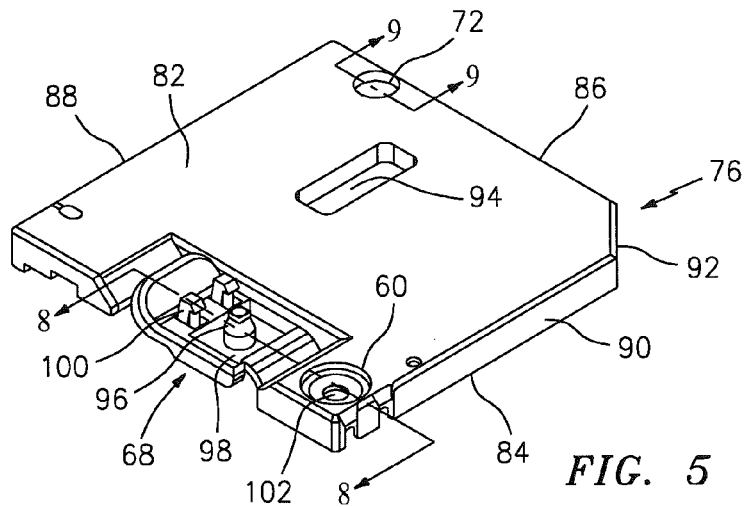
FIG. 5 is a perspective view of a top panel of an embodiment of the present cartridge.
Figure 9:
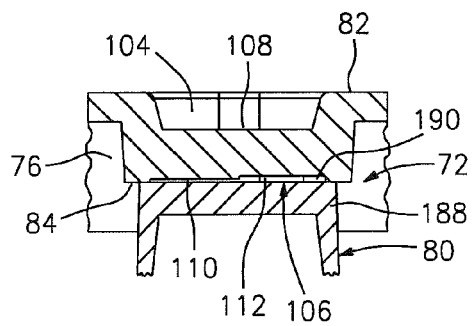
FIG. 9 is a partial sectional view of the top panel of FIG. 5, cut along sectional line 9-9.

FIG. 9 shows a partial sectional view of a secondary analysis chamber 72 embodiment, sectioned along line 9-9 depicted in FIG. 5. The sectional view shows an outer pocket 104 formed in the top panel outer surface 82 and a chamber pocket 106 partially formed in the inner surface 84 of the top panel 76. The two pockets 104, 106 are separated by a portion of the top panel 76 having a planar upper surface 108, and a pair of lower surfaces 110, 112 that are separated from the planar upper surface 108 by different distances. When the base panel 80 is attached to the top panel 76 in the region of the secondary analysis chamber 72 (e.g., by adhesion), a pedestal 188 extending out from the base panel 80 closes the chamber pocket 106 (other than a passage from the secondary channel 64 into the secondary analysis chamber 72), and the two different lower surfaces 112 give the secondary analysis chamber 72 two sections of different height.

Figure 19:
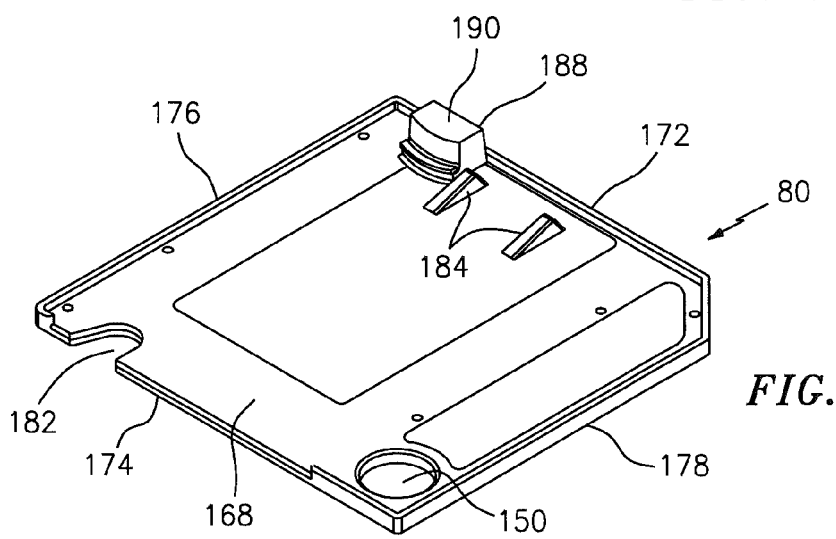
FIG. 19 is a perspective view of a base panel of an embodiment of the present cartridge.

Referring to FIGS. 10-16, an embodiment of the center panel 78 includes a top surface 114, a bottom surface 116, a front edge 118, a first side edge 120, a second side edge 122, a notch edge 124, an analysis chamber window 126, at least one tray clip 128, a pair of lateral tray guides 130, a pair of tray arm locators 132, a fluid actuator port 66, a chamber interface post 134, and a passage 133 extending between the secondary channel 64 and the chamber interface post 134 (referred to hereinafter as the "dispense tube 133"). The perimeter edges of the center panel 78 (i.e., the front edge 118, the first side edge 120, the second side edge 122, and the notch edge 124) are configured to match the counterpart edges of the top panel 76. In the embodiment shown in FIGS. 10 and 11, the center panel 78 includes an aperture 136 for receiving a portion of the secondary analysis chamber 72 (e.g., pedestal 88 as shown in FIG. 19) and a portion of the excess sample reservoir 74. The center panel 78 may be made from a polymeric material; e.g., a colored or opaque Lexan® brand polycarbonate.

Figure 18:
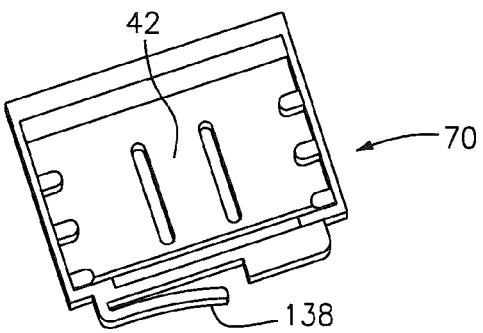
FIG. 18 is a perspective view of a tray including a biasing member.

The tray clip 128 is operable to selectively retain the tray 70 within the cartridge 40; and/or create a biasing force against the tray 70 to resist a certain amount of tray 70 travel relative to the cartridge 40, as will be explained below. In alternative embodiments, a biasing member independent of the tray clip 128 can be used to create the biasing force against the tray 70. For example, FIG. 18 illustrates a tray 70 embodiment having a cantilevered spring arm 138 extending out from an edge of the tray 70. In that embodiment, the spring arm 138 attached to the tray 70 may act against another surface in the cartridge 40 to create the biasing force when deflected. The present cartridge 40 is not limited to including a single tray clip 128, or one that is attached to the center panel 78, or the spring mechanism examples shown in FIGS. 10 and 18. In some embodiments, the cartridge 40 does not include structure that biases the tray 70 relative to the rest of the cartridge 40.

Figure 10:
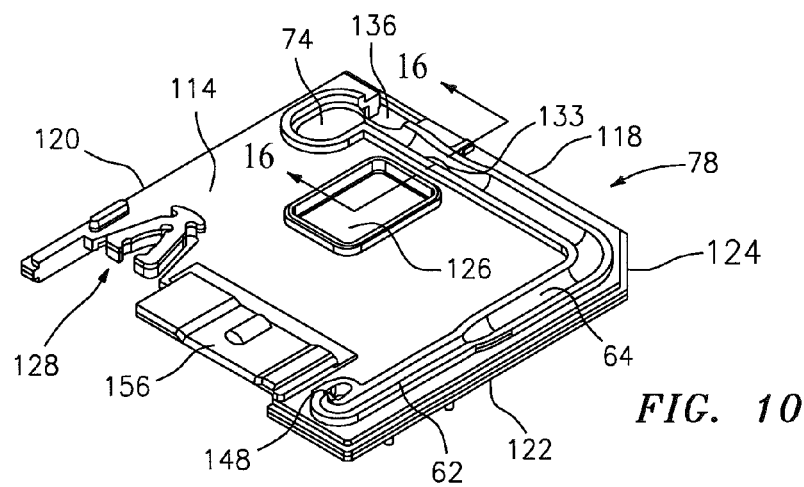
FIG. 10 is a perspective view of a center panel of an embodiment of the present cartridge.
Figure 11:
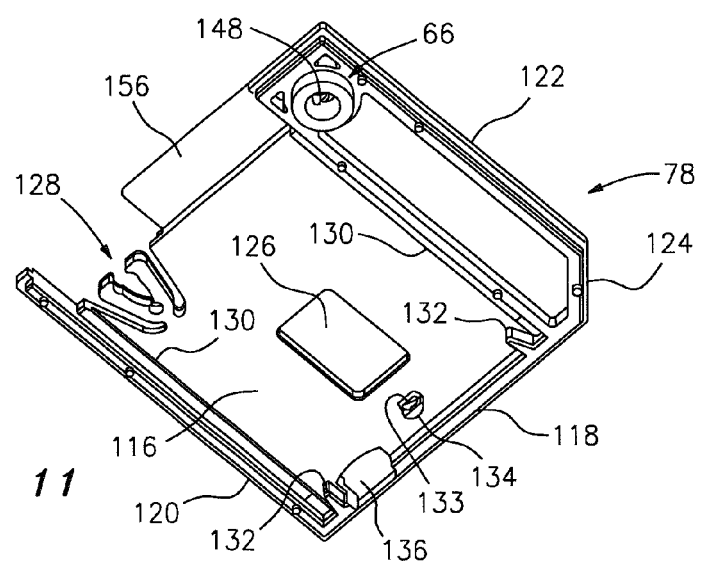
FIG. 11 is a perspective view of the center panel of FIG. 10, showing the opposite surface of the panel.

In the embodiment shown in FIGS. 10-12, the center panel 78 includes a single V-shaped tray clip 128 embodiment. The V-shaped tray clip 128 includes a first arm 140 and a second arm 142, both cantilevering outwardly from the body of the center panel 78, and a center void 144 disposed there between. The center void 144 is accessible via an opening formed between distal ends of the arms 140, 142, which ends are shaped to at least partially enclose the center void 144. As will be explained below, the arms 140, 142 are configured to deflect an amount to receive a clip post 146 through the opening and into the center void 144. The distal ends of the arms 140, 142 selectively maintain the clip post 146 within the center void 144. The V-shaped clip 128 is an example of a retention structure that can be used to selectively retain and/or bias the tray 70 within the cartridge 40. The present cartridge is not limited to this embodiment.

The fluid actuator port 66 is configured to engage a sample motion system 56 incorporated with the analysis device 44 (see FIG. 1) and to permit a fluid motive force (e.g., positive air pressure and/or suction) to access the cartridge 40 to cause the movement of fluid sample within cartridge 40. The fluid actuator port 66 is in fluid communication with the initial channel 62 via a passage 148 (see FIG. 11) extending between the fluid actuator port 66 and the initial channel 62. In the embodiment shown in FIGS. 11 and 13, the fluid actuator port 66 is a raised column with a central port extending out from the bottom surface of the center panel 78. In the assembled cartridge 40, the raised column is accessible through an aperture 150 disposed in the base panel 80 (see FIGS. 19 and 20). Prior to use, the fluid actuator port 66 may be covered by a rupturable seal material 152 (e.g., adhesive tape, etc.; see FIG. 4). The sample motion system 56 of the analysis device 44 includes structure that can access the fluid actuator port 66 (e.g., a probe operable to pierce the rupturable seal material) and thereby create fluid communication between sample motion system 56 and the initial and secondary channels 62, 64. The present cartridge 40 is not limited to this particular fluid actuator port embodiment.

In FIGS. 10, 12, 14, and 15, the center panel top surface 114 is shown, including the passage 148 between the initial channel 62 and the fluid actuator port 66, the dispense tube 133, a capillary flow stop 154 (see FIG. 14), the analysis chamber window 126, the aperture 136 for receiving a portion of the secondary analysis chamber 72, the portion of the excess sample reservoir 74, the V-shaped tray clip 128, and a pad 156 for supporting the port cap 68. FIG. 15 illustrates an embodiment of the dispense tube 133 that has a first end (at the intersection with the channel 64) and a second end (at the opposite end) and that is elongated into a slot-like configuration having a major axis 158 and a minor axis 160. The minor axis 160 is sized to promote capillary force movement of the sample through the dispense tube 133. The major axis 158 is sized to facilitate sample transfer to the analysis chamber 42 as will be described below. The dispense tube 133 embodiment shown in FIG. 15 is a preferred embodiment for at least the reason that it facilitates the creation of an advantageous sample bolus for transfer to the analysis chamber 42. The slotted configuration also helps to eliminate wetting of the sample on the top of the analysis chamber 42, and decreases the pressure required to pass the sample through the dispense tube 133. The present cartridge 40 is not, however, limited to any particular dispense tube 133 configuration.

In FIGS. 11, 13, and 16, the center panel bottom surface 116 is shown, including the fluid actuator port 66, the passage 148 between the fluid actuator port 66 and the initial channel 62, the chamber interface post 134, the dispense tube 133, the analysis chamber window 126, the aperture 136 for receiving a portion of the secondary analysis chamber 72, the lateral tray guides 130, and the tray arm locators 132.

Figure 17:
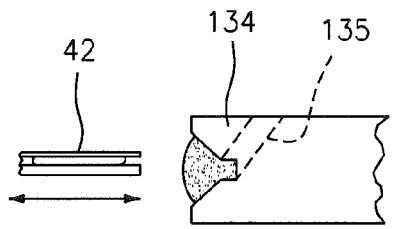
FIG. 17 is a diagrammatic view of an interface between a cartridge channel configured to produce a sample bulge and an analysis chamber.

Referring to FIG. 16, an embodiment of the chamber interface post 134 includes a top guide surface 162, a rear passage surface 164, and a passage bottom surface 166. The orientation of the top guide surface 162 and the passage bottom surface 166 is such that it appears that a section of the dispense tube 133 has been removed. The passage bottom surface 166 is oriented to gravitationally support at least a portion of a bulging sample bolus and thereby facilitate the extension and maintenance of the bolus out from the post 134 during handling of the sample within the analysis device 40. In an alternative embodiment, the chamber interface post 134 (see FIG. 17) has a V-shaped slot intersecting with a passage 135 from the secondary channel 64. As will be explained below, these are examples of preferred analysis chamber interfaces that allow selective direct contact between a sample bolus and the analysis chamber 42, and in particular are interfaces that facilitate the creation of a bulging sample bolus 232 directed toward the sample entry edges 216 of the chamber. The present cartridge 40 is not limited to these chamber interface post embodiments, however. For example, U.S. Patent Application Ser. No. 61/470,142 filed Mar. 31, 2011, which is hereby incorporated by reference in its entirety, discloses alternative interfaces between the analysis chamber 42 and a passage extending from a channel within the cartridge 40.

Figure 20:
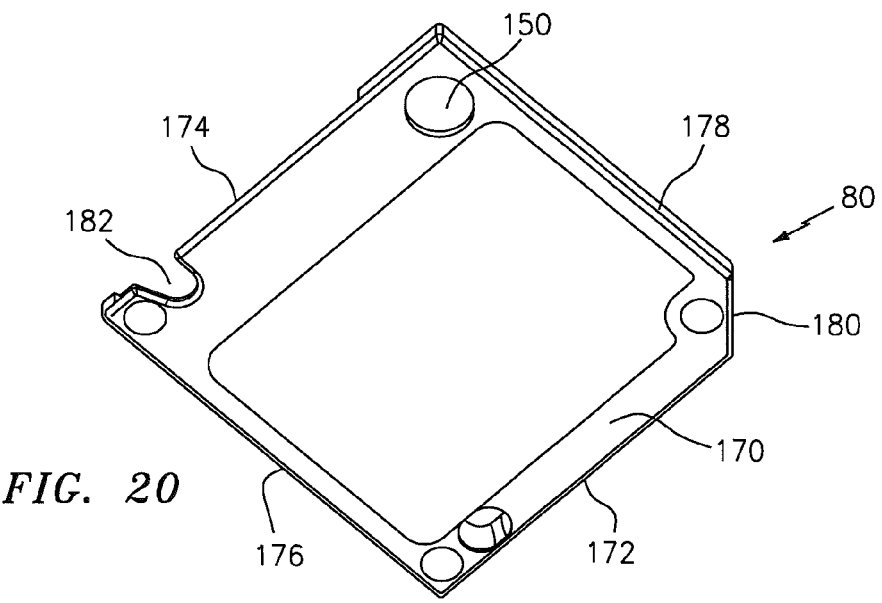
FIG. 20 is a perspective view of the base panel of FIG. 19, showing the opposite surface of the panel.

Referring to FIGS. 19 and 20, an embodiment of the base panel 80 includes an inner surface 168, an outer surface 170, a front edge 172, a tray edge 174, a first side edge 176, a second side edge 178, a notch edge 180, a tray actuator slot 182, a pair of chamber ramps 184, and the aperture 150 for receiving the fluid actuator port 66. The base panel 80 may be made from a polymeric material; e.g., a transparent Lexan® brand polycarbonate. In the embodiment shown in FIG. 19, a pedestal portion 188 of the secondary analysis chamber 72 extends outwardly from the inner surface 168 of the base panel 80. The top surface 190 of the pedestal 188 forms the base of the secondary analysis chamber 72, which base combines with the chamber pocket 106 formed in the top panel 76 to form the secondary analysis chamber 72 (see also FIG. 9).

Figures 21, 22:
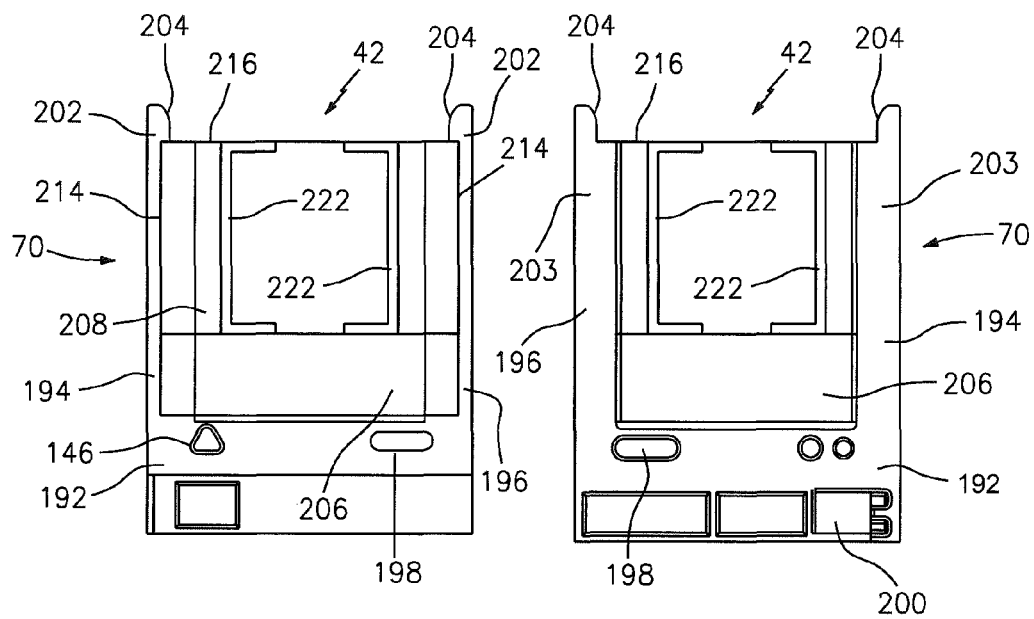
FIG. 21 is a planar view of a tray of an embodiment of the present cartridge.
FIG. 22 is a planar view of the tray of FIG. 21, showing the opposite surface of the tray.
Figure 23:
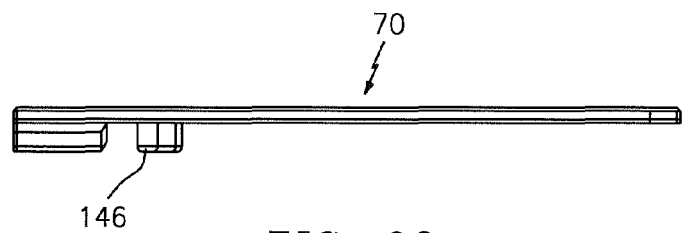
FIG. 23 is a side view of the tray of FIG. 21.

Referring to FIGS. 21 and 22, the tray 70 includes a frame sized to support the analysis chamber 42. For embodiments where the sample disposed within the chamber 42 will be subjected to light transmittance, the tray 70 includes a centrally located opening through which the chamber 42 can be imaged. An example of an acceptable tray 70 embodiment is shown in FIGS. 21-24. In that embodiment, the tray 70 includes a cross member 192, a first arm 194 and second arm 196 extending outwardly from the cross member 192, a clip post 146, one or more alignment features 198 (e.g., apertures), at least one actuator interface 200 (e.g., cavity), and an analysis chamber 42. The clip post 146 extends outwardly from a surface of the cross member 192, and the one or more alignment features 198 extend through the cross member 192. The first and second arms 194, 196 extend parallel to, and are separated from, one another. The first and second arms 194, 196 each have a top surface 202, bottom surface 203, and a locator surface 204 located proximate a distal end of the arm. In alternative embodiments, a second cross member (not shown) may be attached to the distal ends of the arms 194, 196 to give the tray 70 additional rigidity. As indicated above, the present cartridge center panel 78 provides tray arm locators 132 that locate and/or support the tray arms 194, 196. The tray 70 may be made from a polymeric material; e.g., a colored or opaque Lexan® brand polycarbonate.

Figure 24:
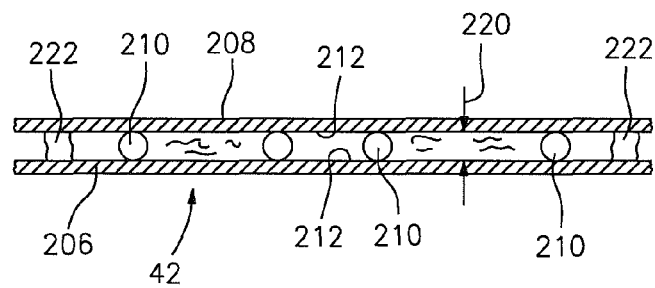
FIG. 24 is a diagrammatic side view of an analysis chamber.
Figure 28:
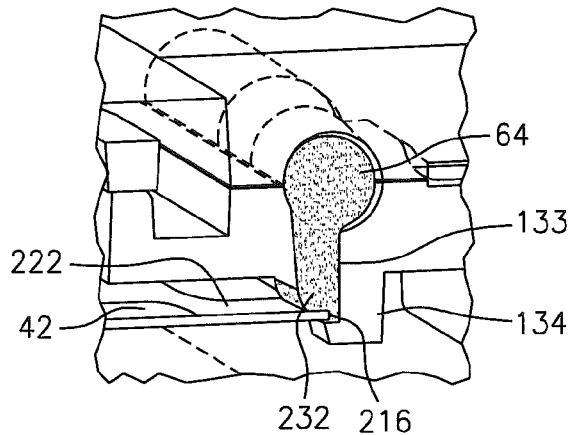
FIG. 28 is the diagrammatic sectional view of the present cartridge shown in FIG. 27, with the edges of the analysis chamber initially engaged with a sample bolus bulging out from the post.

In the embodiment shown in FIGS. 21, 22, and 24, the analysis chamber 42 includes a base chamber panel 206, an upper chamber panel 208, and a plurality of separators 210 disposed there between. At least one of the chamber panels 206, 208 has a transparent region. Preferably, at least a portion of both the upper and lower chamber panels 206, 208 are transparent to light (e.g., transparent regions aligned with one another for light transmittance there through). Each chamber panel 206, 208 has an interior surface 212, a pair of lateral edges 214, and a sample entry edge 216. When assembled, the interior surfaces of the base chamber panel 206 and the upper chamber panel 208 face toward each other, separated from one another by a distance referred to as the "chamber height" 220. In the embodiment shown in FIGS. 21 and 22, the sample entry edges 216 are aligned with one another. In other embodiments, the base chamber panel 206 may extend out beyond the sample entry edge 216 of the upper chamber panel 208. In some embodiments, the chamber height 220 is accurately, uniformly defined by geometric and physical properties of the separators 210 and the chamber panels 206, 208 and is sized to enable capillary forces to draw the sample throughout the chamber 42, as will be described below. In the embodiment shown in FIG. 24, the interior surfaces 212 are parallel one another. The present analysis cartridge 40 is not, however, limited to a parallel configuration; e.g., the analysis chamber height 220 may vary in regions of the chamber 42, including a sloped configuration. In some embodiments, larger diameter separators 210 may be positioned in close proximity to the sample entry edges 216 to flare open the sample entry edges 216 to facilitate the entry of sample into the analysis chamber 42, and/or to separate constituents within the sample. One or both of the interior surfaces 212 within the analysis chamber 42 may be coated with a hydrophilic material to facilitate sample travel within the chamber. The exterior surface of one or both of the upper chamber panel 208 and the base chamber panel 206 may be partially or completely coated with a substance (e.g., a hydrophobic coating) to inhibit wetting of the sample on the exterior surface.

In some embodiments, the analysis chamber 42 includes one or more lateral boundaries 222 disposed between the interior surfaces 212 of the chamber panels 206, 208. The lateral boundaries 212 contain the lateral spread of the sample between the interior surfaces 212; e.g., a lateral boundary 222 may be formed by a hydrophobic coating applied to one or both interior surfaces 212, or by a bead of adhesive (or other formable) material extending between the interior surfaces 212, or by a physical configuration that stops lateral capillary flow of the sample. A bead of adhesive material provides the advantage of also attaching the chamber upper panel 208 to the base chamber panel 206. The lateral boundaries 222 can be used to define a plurality of sub-chambers within the analysis chamber 42; e.g., different chambers configured for different analyses of the sample. In the embodiment shown in FIG. 21, the analysis chamber 42 includes a pair of U-shaped lateral boundaries 222 formed by adhesive beads that together create an entrance opening 224 contiguous with the chamber panel sample entry edges 216, and a rear opening 226 to a single chamber 42. FIG. 25 illustrates an alternative embodiment wherein the lateral boundaries 222 are positioned to create two separate chambers 42a, 42b, the entrance to each contiguous with that of the other. One or both chambers 42a, 42b also has a reduced area rear opening 226a, 226b. The term "reduced area" is used herein to describe an opening other than the entrance opening through which the sample is introduced into the analysis chamber 42, which opening has a dimension across that is less than the entrance opening; e.g., FIG. 26 illustrates an entrance opening 224 having a dimension "X", and a rear opening 226 having a dimension "Y", where X>Y. FIG. 26 illustrates a single chamber 42 configuration, wherein lateral boundaries 222 for a circuitous path to a rear opening 226. The reduced area rear opening 226 and/or circuitous path thereto inhibit the exposure of the leading edge of the sample within the chamber 42 to ambient air and thereby decrease the possibility that sample on, or proximate, the leading edge of the sample will be subject to evaporation. The configurations of the lateral boundaries 222 depicted in FIGS. 21, 22, 25, and 26 are examples of chamber lateral boundaries 222 and the present cartridge 40 is not limited to these examples. The present cartridge 40 may also include one or more small bodies (e.g., "dots") of adhesive extending between the interior surfaces of the chamber 42, where the term "small" is used to describe a cross-sectional area that is individually and collectively insignificant relative to the cross-sectional area of the analysis chamber 42, and therefore does not affect the analysis at hand.

Referring to FIG. 24, at least three separators 210 are disposed within the analysis chamber 42, in contact with both the chamber base panel 206 and the chamber upper panel 208. In a preferred embodiment, the separators 210 are structures independent of both the base chamber panel 206 and the upper chamber panel 208. The separators 210 may be disposed in random distribution with an inter-separator spatial density (i.e., distances between adjacent separators) sufficient to ensure an acceptably uniform chamber height 220 between the chamber panel interior surfaces 212.

At least one of chamber panels 206, 208 or the separators 210 is sufficiently flexible to permit the chamber height 220 to approximate the mean height of the separators 210. The relative flexibility provides an analysis chamber 42 having a substantially uniform height despite the possibility of minor geometric variations in the separators 210 due to manufacturing tolerances of the separators. For example, in those embodiments where the separators 210 are relatively flexible, the larger separators 210 compress (as a result of sample fluid exerting capillary forces on the chamber panels) to allow most separators 210 to contact the interior surfaces 212 of both panels 206, 208, thereby making the chamber height 220 substantially equal to the mean separator diameter. Alternatively, the upper chamber panel 208 may be formed to be more flexible than the separator 210s. In this embodiment, the upper chamber panel 208 will overlay the separators 210 and to the extent that a particular separator is larger than the surrounding separators, the chamber upper panel 208 will flex around the larger separator in a tent-like fashion; e.g., deflect around the larger separator. In this manner, although small local areas of the chamber 42 will deviate from the mean chamber height, the mean height of the chamber regions (including the tented areas) will collectively equal the mean separator 210 diameter with a high degree of accuracy. As indicated above, the capillary forces exerted by the sample provide the force necessary to compress the separators 210, or one of the chamber panels 206, 208. Examples of acceptable separators 210 include polystyrene spherical beads that are commercially available, for example, from Thermo Scientific of Fremont, Calif., U.S.A., catalogue no. 4204A, in four micron (4 μm) diameter. An example of an acceptable analysis chamber 42 configuration is described in U.S. Patent Publication No. 2007/0243117, which is hereby incorporated by reference in its entirety.

Examples of acceptable chamber panel materials include transparent plastic film, such as acrylic, polystyrene, polyethylene terphthalate (PET), cyclic olefin polymer (COP), cyclic olefin copolymer (COC), or the like. In those embodiments where the upper chamber panel 208 is designed to flex when subjected to capillary forces, an upper chamber panel 208 made of PET, having a thickness of approximately twenty-three microns (23μ) provides acceptable flexibility.

The analysis chamber 42 is typically sized to hold about 0.2 to 1.0 μl of sample, but the chamber 42 is not limited to any particular volume capacity, and the capacity can vary to suit the analysis application. The chamber 42 is operable to quiescently hold a liquid sample. The term "quiescent" is used to describe that the sample is deposited within the chamber 42 for analysis, and is not purposefully moved during the analysis. To the extent that motion is present within the blood sample residing within the analysis chamber 42, it will predominantly be due to Brownian motion of the blood sample's formed constituents, which motion is not disabling of the use of this invention.

In some embodiments of the present cartridge 40, one or more reagents (e.g., heparin, EDTA, etc.) are deposited within the initial channel 62. The reagents may also be deposited in the other areas (e.g., collection port 60, secondary channel 64, analysis chambers, etc.).

The cartridge 40 components described above are assembled to form a unitary cartridge 40. The top panel 76 is attached (e.g., by laser welding) to the center panel 78 such that portions of the inner surface 84 of the top panel 76 are fixed to portions of the top surface 114 of the center panel 78. The initial channel 62, secondary channel 64, and the excess sample reservoir 74 are formed by the respective portions in the top panel 76 and center panel 78 being attached to one another. The inner surface 168 of the base panel 80 is also attached to the bottom surface of the center panel 78. The assembled top panel 76, center panel 78, and base panel 80 collectively form a pocket 228 (see FIG. 3) for receiving the tray 70. The present cartridge 40 is not limited to any particular form of attachment between the panel components (e.g., welding, adhesives, mechanical fasteners, etc.) or any particular number of components; e.g., the cartridge may include fewer or more components that provide the functions described above.

In those embodiments that include the secondary analysis chamber 72 embodiment described above, the top panel 76 is also attached to the base panel 80; e.g., the pedestal 188 extends outwardly from the base panel 80, extends through the center panel 78, and is attached to the inner surface 84 of the top panel 76, positioned to close the chamber pocket 106 disposed in the top panel 76, except for the fluid passage entry into the secondary analysis chamber 72.

Referring to FIG. 2, as indicated above the initial channel 62 and the secondary channel 64 may be funned by the joining of the respective portions in the top panel 76 and center panel 78. The cross-sectional area of the initial channel 62 is such that capillary forces acting on the sample will draw the sample through the initial channel 62. The portions that form the initial channel 62 may be specifically sized to create a predetermined initial channel volume, which volume is used to determine the correct amounts of reagents (e.g., anticoagulants, colorants, etc) to be mixed with the sample. At the interface 63 between the initial channel 62 and the secondary channel 64, the cross-sectional area of the secondary channel 64 is such that capillary forces will not draw liquid sample out of the initial channel 62 and into the secondary channel 64.

Referring to FIG. 35, in some embodiments the initial channel 62 may include a section 65 of decreased cross-sectional area (e.g., a "constricted section 65") located contiguous with the interface 63 between the initial channel 62 and the secondary channel 64. Capillary forces acting on fluid sample disposed within the initial channel 62 will cause the fluid sample to fill the constricted section 65, and the increased cross-sectional area of the secondary channel 64 will stop further capillary based travel. The dimensions of the constricted section 65 are chosen such that the cartridge 40 can be tilted to a position where the constricted section 65 has a gravitational vertical component (with the secondary channel 64 disposed gravitationally below the constricted section 65) and fluid sample within the constricted section 65 will not travel from the constricted section 65 into the secondary channel 64 absent an externally applied motive force acting on the fluid. In some embodiments, the constricted section 65 may be sized to prevent fluid from constricted section 65 in some, but not all, positions having a gravitational vertical component. In other embodiments, the constricted section 65 may be sized to prevent fluid from constricted section 65 in all positions having a gravitational vertical component. The specific dimensions of the constricted section 65 necessary to prevent fluid travel in such an orientation will depend upon the specific fluid sample being analyzed; e.g., the dimensions of the constricted section 65 within a cartridge 40 designed for plasma analysis may be different from those used in a cartridge 40 designed for whole blood analysis.

In some embodiments, the secondary channel 64 includes a channel configuration operable to create an increased pressure region within the secondary channel 64. The increased pressure region can be used to facilitate fluid movement out of the mixing channel 64. The channel configuration can, for example, include a region of constricted cross-sectional area 230 (e.g., see FIG. 15) that is substantially aligned with the dispense tube 133. In the embodiment shown in FIGS. 2-4, the region of constricted area 230 includes one side of the secondary channel 64 extending along a straight line, and the other wall curving outwardly toward the straight side to decrease the cross-sectional area of the secondary channel 64 there between. A constricted area region 230 is an example of channel configuration that can be used to facilitate fluid movement, and the present cartridge 40 is not limited to this embodiment. The secondary analysis chamber 72 and the excess sample reservoir 74 are in fluid communication with the secondary channel 64 on the side of the constriction opposite the initial channel 62.

The analysis chamber 42 can be formed and attached to the tray 70 prior to inserting the tray 70 into the cartridge pocket. The separators 210 and lateral boundaries 222, if used, are disposed between the chamber panels 206, 208, and the base chamber panel 206 is attached to the top surface 202 of each arm 194, 196. The sample entry edges 216 of the chamber panels 206, 208 may be aligned with one another, and located proximate the distal ends of the tray arms 194, 196.

When the tray 70 is received in the cartridge pocket 228, the top surface of each arm 194, 196 faces the bottom surface 116 of the center panel 78. The lateral tray guide surfaces 130 of the center panel 78 guide the arms 194, 196 of the tray 70 within the pocket 228. When the tray 70 is slid into the cartridge pocket 228 enough, it will reach and is held in a predetermined "park" position within the pocket 228.

Before the tray 70 can be moved into the "park" position, the clip post 146 extending out from the tray 70 will encounter the tray clip 128 attached to the center panel 78. The clip post 146 deflects the distal ends of the tray clip arms 140, 142 as it passes through the opening and into the center void 144 of the V-shaped tray clip 128. Once the clip post 146 is inside the center void 144, the arms 140, 142 return toward their original position, thereby retaining the clip post 146 within the center void 144, and maintaining the tray 70 in the "park" position. In some cartridge 40 embodiments, when the tray 70 is in the park position, the sample entry edges 216 of the chamber panels 206, 208 are in close proximity to the chamber interface post 134, but are separated from the post 134 enough such that a bolus of sample extending out from the chamber interface post 134 will not contact the sample entry edges 216 of the chamber panels. In other cartridge embodiments, when the tray is in the park position, the sample entry edges 216 of the chamber panels 206, 208 are in contact with the chamber interface post 134, or sufficiently close to the post 134 to permit sample transfer. As indicated above, the described V-shaped tray clip 128 and clip post 146 combination is an acceptable tray retaining (and/or biasing) mechanism. The present cartridge 40 is not, however, limited to this particular clip embodiment. In any of the above described embodiments, the tray 70 may or may not be biased within the cartridge 40. In addition, the cartridge 40 may be configured to allow the tray 70 to be partially or completely removed from the pocket 228 within the cartridge 40.

Operation:

A biologic fluid sample (e.g., a whole blood sample) is deposited in the collection port 60 of the cartridge 40. The sample is drawn through the drain tube 102 and into the initial channel 62 at least in part by capillary action. The sample travels within the initial channel 62 until the leading edge of the sample encounters the interface between the initial channel 62 and the secondary channel 64. The collection port cap 68 is engaged with the collection port 60 and the stopper 96 seals the drain tube 102. As a result, a predetermined volume of sample is disposed in the initial channel 62. To the extent that there may be any sample left in the collection port 60 after the stopper 96 seals the drain tube 102, the absorbent pad provided with the cap absorbs that sample and prevents leakage. In those embodiments of the present cartridge 40, where one or more reagents (e.g., heparin, EDTA, colorant) are disposed in the initial channel 62 or elsewhere in the cartridge 40 for addition to the sample, the defined volume of sample collected within the initial channel 62 ensures that a defined amount of reagent is mixed with the sample. As the sample passes through the initial channel 62, the reagents are admixed with the sample.

The transparent top panel 76 allows the end-user to visually detect whether the initial channel 62 is full of sample. As will be described below, the tray/chamber is typically located in the park position during acquisition of sample into the cartridge 40.

The "loaded" cartridge 40 can subsequently be placed into the analysis device 44. The correct orientation of the cartridge 40 within the analysis device 44 is facilitated by asymmetrical locating features of the cartridge 40 such as the notched edge. After the end-user loads the cartridge 40 into the analysis device 44, the analysis device 44 locates and positions the cartridge 40 for further processing. At the time the cartridge 40 is loaded into the analysis device 44, or sometime thereafter, a mechanism (e.g., a probe) from the sample motion system 56 engages the fluid actuator port 66 of the cartridge 40 (e.g., by rupturing the membrane), and creates fluid communication between the bidirectional fluid actuator and the initial channel 62. The capillary flow stop 154 (see FIG. 14) disposed between the passage 148 from the fluid actuator port 66 and the initial channel 62 prevents sample flow back into the fluid actuator port 66. The analysis device 44, via the bidirectional fluid actuator, is operable to produce fluid motive forces that can move fluid sample (e.g., a sample bolus) within channels 62, 64 disposed in the cartridge 40 in either axial direction (i.e., back and forth). U.S. patent application Ser. No. 13/077,476 (incorporated by reference above), describes an analysis device 44 that includes a bidirectional fluid actuator that is acceptable for use with the present cartridge 40.

In the case of a whole blood sample that was collected and not immediately analyzed, constituents within the sample bolus (e.g., RBCs, WBCs, platelets, and plasma) can settle and become stratified (or otherwise non-uniformly distributed) over time. In such cases, there is considerable advantage in manipulating the sample bolus prior to analysis so that the constituents are substantially uniformly distributed within the sample. In addition, in many applications there is also considerable advantage in uniformly mixing reagents with the sample bolus. To create a substantially uniform distribution of constituents and/or reagents within the sample bolus, the analysis device 44 provides a signal to the bidirectional fluid actuator to provide fluid motive force adequate to move the sample bolus residing within the initial channel 62; e.g., forwards, backwards, or cyclically within the initial channel 62, or combinations thereof.

Once the sample residing within the initial channel 62 is mixed sufficiently to create a substantially uniformly mixed sample, the bidirectional fluid actuator may be operated to move the sample bolus from the initial channel 62 to the secondary channel 64. Once the sample bolus is located within the secondary channel 64, the sample bolus can be actuated according to the requirements of the analysis at hand For example, in those analyses where it is desirable to have the sample admix with reagent "A" before mixing with a dye "B", an appropriate amount of reagent "A" (e.g., an anticoagulant—EDTA) can be positioned upstream of an appropriate amount of dye "B" within the channel. The configuration of the channels within the cartridge 40 permits mixing at a plurality of locations. Feedback positioning controls can be used to sense (e.g., optical sensors sensing through the transparent top panel 76) and control sample bolus positioning within the initial channel 62 and/or the secondary channel 64.

Subsequently, the sample motion system 56 is operated to move the sample bolus forward in the secondary channel 64 for transfer into the analysis chamber 42. The sample bolus is moved into engagement with the dispense tube 133. As indicated above, some cartridge 40 embodiments include a constricted region 230 in the secondary channel 64 aligned with the dispense tube 133. Such a constricted region 230 can be used to create an elevated pressure region within the sample bolus to facilitate transfer of sample from the secondary channel 64 to the chamber interface post 134. The present cartridge 40 is not limited to employing pressure, capillary forces, or gravity to transfer the sample to the post 134, and may use combinations thereof.

Referring to FIGS. 27-31, the sample bolus travels within the dispense tube 133 until it reaches the opening formed in the chamber interface post 134. In some embodiments, the tray 70 and analysis chamber 42 may reside in the park position when the sample bolus is traveling within the dispense tube 133. In other embodiments, the tray 70 may be partially or completely removed from the cartridge 40 when the sample bolus is traveling within the dispense tube 133. When the bolus reaches the bottom of the dispense tube 133, a portion 232 of the sample bolus will bulge outwardly from the dispense tube 133.

Figure 32:
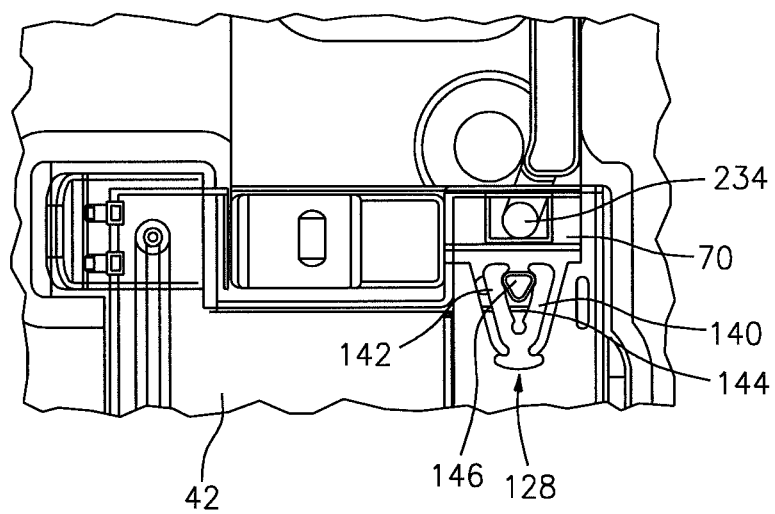
FIG. 32 is a planar diagrammatic view of a tray actuating device engaged with a tray in an embodiment of the present cartridge, illustrating the tray in the "park" position.

FIG. 27 diagrammatically illustrates a sectional view (e.g., the analysis chamber 42 sectioned approximately in half) of an embodiment wherein the tray 70 is in the "park" position and the sample entry edges 216 of the chamber panels are separated from, and therefore not engaged with, the sample bolus 232. The planar view of FIG. 32 shows the tray 70 in the park position with a lever 234 portion of a tray actuation device 57 engaged with the tray 70. In such embodiments, transfer of sample to the analysis chamber 42 will not occur in the park position. As indicated above, however, in some embodiments the sample entry edges 216 of the chamber panels 206, 208 may be in contact with the chamber interface post 134 and will allow (or sufficiently close to the post 134 to permit) sample transfer from the bolus when the tray 70 is in the park position.

Figure 33:
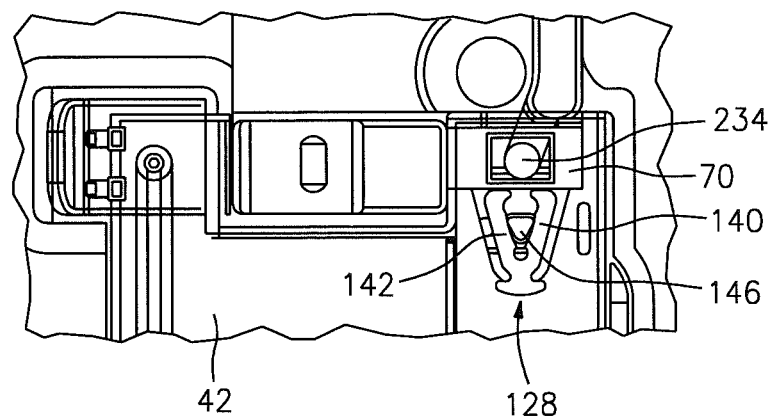
FIG. 33 is the planar diagrammatic view of FIG. 32, illustrating the tray in a bolus engaged position.
Figure 34:
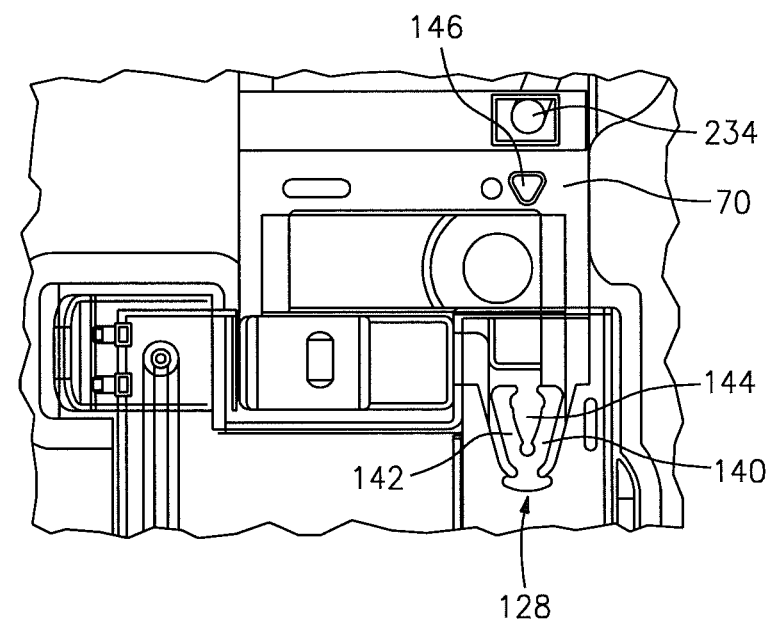
FIG. 34 is the planar diagrammatic view of FIG. 32, with the tray actuating device engaged with a tray and the tray partially removed from the cartridge.

FIGS. 28-30 and 33 illustrate the tray 70 moved into a bolus engaged position within the cartridge 40 (which may be a park position in some embodiments) by a lever 234 portion of the tray actuation device 57. FIG. 33 shows an embodiment of the clip post 146 disposed forward in the center void 144, acting against the tray clip arms 140, 142 and causing the arms to deflect outwardly. In this embodiment, the clip arms 140, 142 provide a biasing force that acts on the tray 70 to bias the tray toward the park position. In alternative embodiments, no biasing force is present (e.g., a tray clip configuration wherein the arms do not deflect). In all embodiments of the V-shaped tray clip 128, the clip 128 is configured such that the clip post 146 may travel within the tray clip 128 a distance great enough so that the sample entry edges 216 can engage with the sample bolus 232. The tray actuation device lever 234, which moved the tray 70 into the bolus engaged position, can be operated to maintain the tray 70 in the bolus engaged position. In those embodiments that include tray arm locators 132 (see FIG. 11), the locators 132 provide positional stops for the tray arms 194, 196 to define relative positions between the sample entry edges 216 of the chamber panels 206, 208 and the chamber interface post 134 when the tray is in the bolus engaged position. In those embodiments that include chamber ramps 184 (see FIG. 19) extending out from the inner surface of the base panel 80, the chamber ramps 184 (see FIG. 19) facilitate positioning of the sample entry edges 216 relative to the chamber interface post 134.

Figure 29:
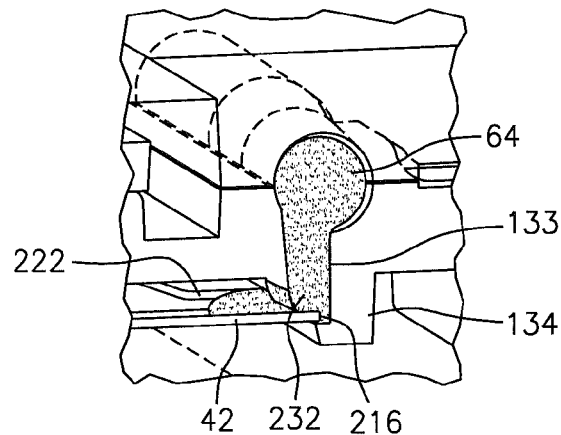
FIGS. 29 and 30 are the diagrammatic sectional view of the present cartridge shown in FIG. 28, showing the edges of the analysis chamber engaged with the sample bolus and the sample loading into the analysis chamber.
Figure 30:
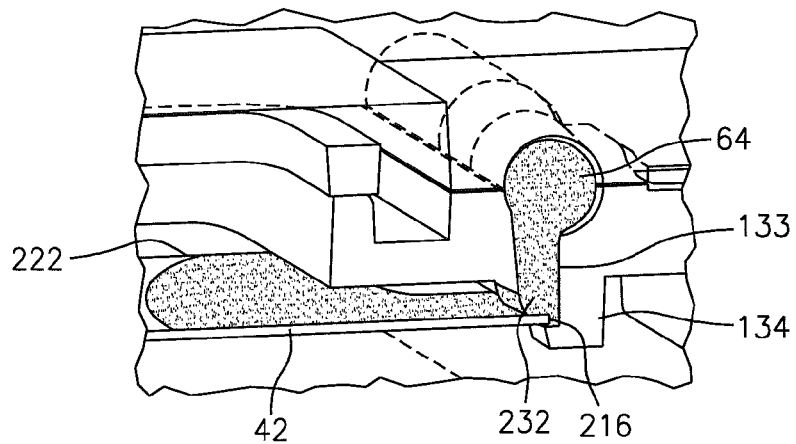

When the tray 70 is in the bolus engaged position, at least a portion of the sample entry edges 216 of the chamber panels are positioned to permit engagement with the sample bolus 232 disposed at the end of the interface post 134; e.g., the sample entry edges 216 of the chamber panels 206, 208 may be in contact with the chamber interface post 134 or may be sufficiently close to the post 134 to permit sample transfer from the bolus extending out from the dispense tube 133. In those embodiments where the analysis chamber 42 includes lateral boundaries 222, the major axis 158 of the dispense tube 133 may be aligned with and approximately equal in length to the chamber entrance 224 defined by the lateral boundaries 222. The present cartridge 40 is not limited to this embodiment, however. FIGS. 29 and 30 show the movement of sample from the bolus 232 into the chamber 42 (e.g., by capillary force), laterally constrained by lateral boundaries 222.

In some embodiments, the analysis chamber 42 may be maintained in the bolus engaged position for a predetermined period of time adequate to transfer an acceptable volume of sample for the analysis at hand. An advantage of the present cartridge 40 with a selectively movable tray 70 is that the sample flow into the analysis chamber 42 can be started at a known point in time. For example, if the initial sample transfer time is known, then the sample transfer can be controlled as a function of time. Alternatively, if the amount of sample within the sample is monitored by sensors, then the sensing function can be coordinated with the initial time; e.g., initial chamber optical values can be determined prior to transfer, sample position within the analysis chamber can be tracked, etc. The analysis chamber windows disposed in the top panel 76 and center panel 78 allow the analysis chamber 42 to be sensed; e.g., sensors sensing through the windows in the top and center panels 76, 78 can be used to determine the position of the sample within the analysis chamber 42. For example, a light source (LED or laser) can be used to illuminate the analysis chamber 42. As the light impinges on the blood sample within the chamber 42, light reflected laterally within the sample illuminates the blood/air interface edges of the sample, causing them to be distinguishable relative to the sample and the air. The distinguished blood/air interface edges can be detected by an optical sensor; e.g., a transmittance or reflectance optical sensor. The present cartridge 40 is not limited to use with such sensors.

Figure 31:
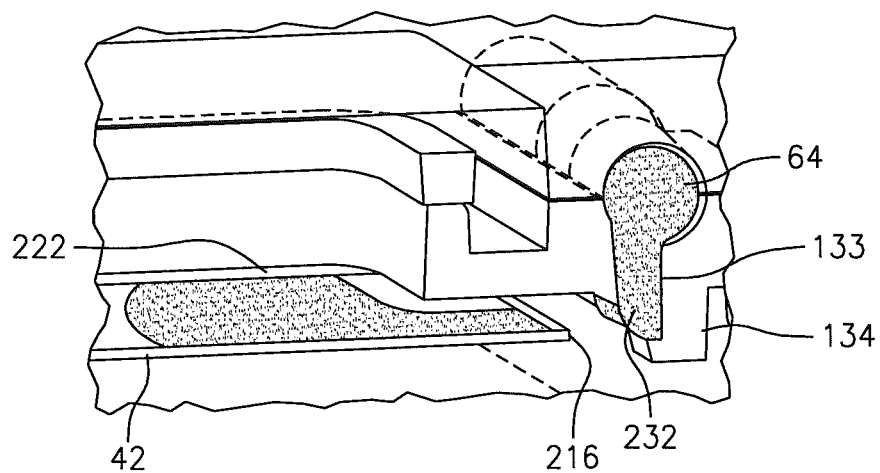
FIG. 31 is the diagrammatic sectional view of the present cartridge shown in FIGS. 28-30, showing the edges of the analysis chamber now disengaged with the sample bolus and a volume of sample loaded in the analysis chamber.

In some embodiments, once an acceptable volume of sample has been transferred to the analysis chamber 42, the tray actuator lever 234 moves the tray 70 back into the park position (or allows the biasing force of the tray clip 128 to do so), thereby causing the sample entry edges 216 of the analysis chamber 42 to disengage from the sample bolus 232 and stop the transfer of sample fluid to the analysis chamber 42. FIG. 31 illustrates an analysis cartridge 40 containing a fluid sample, disengaged with the sample bolus 232.

Once the analysis chamber 42 is filled with sample, the tray 70 is operable to be moved partially or completely out of the cartridge 40 via the tray actuation device 57 to an analysis position, where at least a portion of the analysis chamber 42 is exposed for imaging by the analysis device 44. Once the imaging is completed, the tray 70 can be moved back into the cartridge 40 into the park position where the clip post 146 and tray clip 128 maintain the tray 70 thereafter. The sample images are subsequently analyzed to produce sample analysis data.

In those embodiments that include a secondary analysis chamber 72, sample drawn into the secondary analysis chamber 72 can be imaged by transmittance through the chamber 72. The secondary analysis chamber 72 described above having two different height sections can be used for sample optical measurements; e.g., differential measurements of optical density, which values can be to determine hemoglobin information for example. The known difference in the chamber sections permits relative measurements in the event the overall height of the secondary chamber sections is not accurately known.

While the invention has been described with reference to an exemplary embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment(s) disclosed herein as the best mode contemplated for carrying out this invention. For example, embodiments of the present cartridge 40 are described above as including an analysis chamber 42 that is mounted so that it can be moved into engagement with a bolus of sample for a given period of time to enable fluid sample transfer to the analysis chamber 42. In alternative embodiments, the cartridge 40 may be configured so that the sample bolus may be moved into engagement with the analysis chamber 42 to permit the transfer of sample there between.

In addition, the present cartridge is described as having numerous features. One or more of these features may represent patentable subject matter alone, or in combination with other features. The present invention is not, therefore, limited to the cartridge embodiment described as including all of these features. For example, the present cartridge is described as having a tray with an analysis chamber attached to the tray. Alternative embodiments of the present cartridge may utilize an analysis chamber positionally fixed relative to the cartridge. As another example, numerous configurations for sample transfer between the cartridge channels and the analysis chamber are described above. These configurations represent structural and operational embodiments of the present cartridge, and the present cartridge is not limited to these particular embodiments. In yet another example, the present cartridge is described above in terms of a particular fluid actuator port for engagement with a sample motion system. The present cartridge is not limited to use with any particular type of sample motion system, and therefore not limited to any particular type of fluid actuator port 66.

What is claimed is:

1. A biological fluid sample analysis cartridge, comprising:
   a collection port;
   at least one channel within the cartridge in fluid communication with the collection port;
   a passage in fluid communication with the at least one channel; and
   an analysis chamber mounted on a tray, which tray is mounted relative to the cartridge and selectively positionable relative to the passage in a first position where the analysis chamber engages a bolus of sample extending out from the passage to permit selective transfer of sample from the bolus to the analysis chamber, and positionable in a second position within the cartridge and in the second position the analysis chamber is separated from the passage.

2. The cartridge of claim 1, wherein the passage includes a first end and a second end, and which first end is in fluid communication with the at least one channel, and which second end is configured to permit the formation of a bolus of sample extending out from the second end.

3. The cartridge of claim 2, wherein the analysis chamber includes a base chamber panel and an upper chamber panel, separated from one another by a chamber height, and each of the panels includes a sample entry edge.

4. The cartridge of claim 3, wherein the sample entry edges of the panels are substantially aligned with one another.

5. The cartridge of claim 3, wherein in the first position the tray is mounted relative to the cartridge so that at least one of the sample entry edges of the analysis chamber engages the bolus of sample extending out from the second end of the passage.

6. The cartridge of claim 2, wherein at least the first end of the passage has a slot configuration with a major axis and a minor axis, wherein the major axis is larger than the minor axis.

7. The cartridge of claim 2, wherein the passage is at least partially disposed within an interface post.

8. The cartridge of claim 7, wherein the interface post includes a surface disposed at the second end of the passage, which surface is oriented to gravitationally support at least a portion of the sample bolus.

9. The cartridge of claim 7, wherein the interface post includes a V-shaped slot intersecting with the second end of the passage.

10. The cartridge of claim 2, wherein the analysis chamber is defined by a base chamber panel, an upper chamber panel, and a plurality of lateral boundaries, and wherein the lateral boundaries than a first opening and second opening, and wherein the first opening is larger than the second opening.

11. The cartridge of claim 10, wherein the base chamber panel has an interior surface, and the upper chamber panel has an interior surface, and at least one of the lateral boundaries contacts both interior surfaces.

12. The cartridge of claim 11, wherein the lateral boundaries are configured to create a circuitous path between the first opening and the second opening.

13. The cartridge of claim 11, wherein the analysis chamber includes a plurality of sub-chambers founed by the lateral boundaries.

14. The cartridge of claim 2, further comprising a secondary analysis chamber in fluid communication with the at least one channel.

15. The cartridge of claim 14, wherein the secondary chamber has a first portion having a first height, and a second portion having a second height, which second height is greater than the first height, and a difference between the two heights is known.

16. The cartridge of claim 2, wherein the at least one channel includes an initial channel in fluid communication with the collection port, and a secondary channel having a first end in fluid communication with the initial channel and a second end in fluid communication with the passage.

17. The cartridge of claim 1, wherein a biasing structure maintains the tray in the second position and in the first position the biasing structure biases the tray toward the second position.

18. The cartridge of claim 17 wherein the tray includes the biasing structure.

19. The cartridge of claim 17, wherein the biasing structure is a tray clip operable to maintain the tray in the second position.

20. The cartridge of claim 19, wherein the tray clip is V-shaped and includes a first arm, a second arm, and a center void disposed between the first and second arms.

21. The cartridge of claim 1, further comprising a fluid actuator port configured to engage a sample motion system and to permit a fluid motive force to access the cartridge to cause the movement of fluid sample within the at least one channel.

22. The cartridge of claim 21, wherein the fluid actuator port includes a rupturable seal material.

23. The cartridge of claim 1, further comprising a cap operable to cover and seal the collection port.

24. The cartridge of claim 1, further comprising an analysis chamber window configured to allow visual inspection of the analysis chamber disposed in the first position.

25. The cartridge of claim 1, wherein the tray is configured to engage an actuator operable to selectively move the tray relative to the cartridge.

26. The cartridge of claim 1, wherein the cartridge includes a pocket configured to receive the tray.

27. The cartridge of claim 26, wherein the tray is configured to engage an actuator operable to selectively move the tray into and out of the pocket.

28. A biological fluid sample analysis cartridge, comprising:
   a collection port;
   at least one channel within the cartridge in fluid communication with the collection port;
   a passage in fluid communication with the at least one channel; and
   an analysis chamber mounted on a tray, which tray is mounted relative to the cartridge and selectively positionable relative to the passage in a first position where the analysis chamber engages a bolus of sample extending out from the passage to permit selective transfer of sample from the bolus to the analysis chamber;
   wherein the passage includes a first end and a second end, and which first end is in fluid communication with the at least one channel, and which second end is configured to permit the formation of a bolus of sample extending out from the second end; and
   wherein the at least one channel includes an initial channel in fluid communication with the collection port, and a secondary channel having a first end in fluid communication with the initial channel and a second end in fluid communication with the passage; and
   wherein the initial channel has a cross-sectional area sized such that sample travels by capillary force within the initial channel and the secondary channel has a cross-sectional area sized such that sample cannot travel by capillary force within the secondary channel.

29. The cartridge of claim 28, wherein the initial channel includes a constricted section adjacent an interface with the secondary channel, and the constricted section is configured such that the cartridge can be oriented with the initial channel gravitationally vertical and fluid within the constricted section will not travel from the constricted section into the secondary channel absent externally applied motive force.

30. The cartridge of claim 2, wherein the at least one channel includes the passage.

* * * * *